(12) United States Patent
Koller et al.

(10) Patent No.: US 10,485,596 B2
(45) Date of Patent: Nov. 26, 2019

(54) LONGITUDINALLY-ADJUSTABLE BONE ANCHORS AND RELATED METHODS

(71) Applicant: Medos International Sarl, Le Locle (CH)

(72) Inventors: Heiko Koller, Waldeck-Alraft (DE); J. Riley Hawkins, Cumberland, RI (US); Christopher Ramsay, Wareham, MA (US)

(73) Assignee: Medos International Sàrl, Le Locle (CH)

( * ) Notice: Subject to any disclaimer, the term of this patent is extended or adjusted under 35 U.S.C. 154(b) by 346 days.

(21) Appl. No.: 15/370,078

(22) Filed: Dec. 6, 2016

(65) Prior Publication Data

US 2018/0153600 A1 Jun. 7, 2018

(51) Int. Cl.
*A61B 17/70* (2006.01)
*A61B 17/86* (2006.01)
(Continued)

(52) U.S. Cl.
CPC ...... *A61B 17/8685* (2013.01); *A61B 17/7032* (2013.01); *A61B 17/864* (2013.01);
(Continued)

(58) Field of Classification Search
CPC . A61B 17/70; A61B 17/7001; A61B 17/7032; A61B 17/7034; A61B 17/7035;
(Continued)

(56) References Cited

U.S. PATENT DOCUMENTS 4,870,957 A * 10/1989 Goble .................. A61B 17/686
623/13.12
5,254,118 A 10/1993 Mirkovic
(Continued)

FOREIGN PATENT DOCUMENTS

DE 10 2014 116776 A1 5/2016
EP 2 826 429 A1 1/2015
WO 2009/118033 A1 10/2009

OTHER PUBLICATIONS

International Search Report and Written Opinion for PCT/US2017/061037, dated Apr. 17, 2018 (25 pages).

*Primary Examiner* — Eric S Gibson
(74) *Attorney, Agent, or Firm* — Nutter McClennen & Fish LLP

(57) ABSTRACT

Longitudinally-adjustable bone anchors and related methods are disclosed herein. The ability to adjust a bone anchor longitudinally can allow the surgeon to bring an implanted bone anchor up to the rod instead of or in addition to bringing the rod down to the bone anchor, which can simplify or eliminate the rod contouring step and reduce or eliminate reduction forces. For example, the surgeon can use a pre-bent rod or put "ideal contours" into a rod, lay the rod across a series of bone anchors, and adjust each bone anchor longitudinally to meet the rod. As another example, coarse adjustment of the fixation system can be achieved by contouring the rod and then fine adjustments can be made by bringing each bone anchor up or down to the rod. Various adjustment mechanisms are disclosed, including bone anchors with telescoping portions and bone anchors with risers or spacers.

21 Claims, 10 Drawing Sheets

(51) Int. Cl.
*A61B 17/00* (2006.01)
*A61B 90/00* (2016.01)

(52) U.S. Cl.
CPC ...... *A61B 17/8605* (2013.01); *A61B 17/8625* (2013.01); *A61B 2017/00867* (2013.01); *A61B 2090/037* (2016.02)

(58) Field of Classification Search
CPC . A61B 17/7037; A61B 17/7038; A61B 17/86; A61B 17/8625; A61B 17/863; A61B 17/864; A61B 17/8685
See application file for complete search history.

(56) References Cited

U.S. PATENT DOCUMENTS

| | | | |
|---|---|---|---|
| 5,380,323 A | 1/1995 | Howland | |
| 5,443,467 A | 8/1995 | Biedermann et al. | |
| 5,545,167 A | 8/1996 | Lin | |
| 5,569,251 A * | 10/1996 | Baker | A61B 17/686 606/281 |
| 6,736,820 B2 | 5/2004 | Biedermann et al. | |
| 6,835,196 B2 | 12/2004 | Biedermann et al. | |
| 6,974,460 B2 | 12/2005 | Carbone et al. | |
| 7,179,261 B2 | 2/2007 | Sicvol et al. | |
| 7,291,151 B2 | 11/2007 | Alvarez | |
| 7,314,467 B2 | 1/2008 | Howland | |
| 7,338,491 B2 | 3/2008 | Baker et al. | |
| 7,404,818 B2 | 7/2008 | Miller et al. | |
| 7,445,627 B2 | 11/2008 | Hawkes et al. | |
| 7,578,833 B2 | 8/2009 | Bray | |
| 7,588,593 B2 | 9/2009 | Aferzon | |
| 7,922,748 B2 | 4/2011 | Hoffman | |
| 8,048,124 B2 | 11/2011 | Chin et al. | |
| 8,083,778 B2 | 12/2011 | Clement et al. | |
| 8,246,658 B2 | 8/2012 | Rezach | |
| 8,277,490 B2 | 10/2012 | Freeman et al. | |
| 8,313,515 B2 | 11/2012 | Brennan et al. | |
| 8,343,200 B2 | 1/2013 | Khanna et al. | |
| 8,414,621 B2 | 4/2013 | Biedermann et al. | |
| 8,480,713 B2 | 7/2013 | Rezach | |
| 8,562,651 B2 | 10/2013 | Metcalf et al. | |
| 8,562,652 B2 | 10/2013 | Biedermann et al. | |
| 8,617,216 B2 | 12/2013 | Brumfield | |
| 8,663,289 B2 | 3/2014 | Schwab | |
| 8,870,925 B2 | 10/2014 | Freudiger | |
| 8,915,945 B2 | 12/2014 | Carson et al. | |
| 9,060,812 B2 | 6/2015 | Timm | |
| 9,089,371 B1 * | 7/2015 | Faulhaber | A61B 17/7035 |
| 9,144,437 B2 | 9/2015 | Matthis et al. | |
| 9,226,777 B2 | 1/2016 | Potash et al. | |
| 9,339,316 B2 * | 5/2016 | Hulliger | A61B 17/84 |
| 9,579,123 B2 | 2/2017 | Faulhaber | |
| 9,615,873 B2 * | 4/2017 | Weiner | A61B 17/68 |
| 2007/0191842 A1 | 8/2007 | Molz et al. | |
| 2008/0045963 A1 | 2/2008 | Abdou | |
| 2008/0177324 A1 * | 7/2008 | Oribe | A61B 17/7037 606/267 |
| 2009/0248088 A1 | 10/2009 | Biedermann | |
| 2009/0264926 A1 | 10/2009 | Taylor et al. | |
| 2010/0049253 A1 | 2/2010 | Miller | |
| 2010/0069913 A1 | 3/2010 | Chirico et al. | |
| 2010/0114174 A1 | 5/2010 | Jones et al. | |
| 2010/0211116 A1 * | 8/2010 | Suh | A61B 17/8033 606/305 |
| 2010/0241170 A1 | 9/2010 | Cammisa et al. | |
| 2010/0249846 A1 | 9/2010 | Simonson | |
| 2011/0106181 A1 | 5/2011 | Rezach et al. | |
| 2011/0288599 A1 | 11/2011 | Michielli et al. | |
| 2012/0059421 A1 | 3/2012 | Aferzon | |
| 2012/0215263 A1 * | 8/2012 | Lee | A61B 17/7037 606/305 |
| 2013/0053901 A1 | 2/2013 | Cormier et al. | |
| 2013/0245697 A1 * | 9/2013 | Hulliger | A61B 17/84 606/281 |
| 2014/0005731 A1 * | 1/2014 | Biedermann | A61B 17/686 606/328 |
| 2014/0066991 A1 * | 3/2014 | Marik | A61B 17/7032 606/279 |
| 2014/0188172 A1 * | 7/2014 | Nichols | A61B 17/7004 606/278 |
| 2014/0228887 A1 | 8/2014 | Raju et al. | |
| 2014/0257411 A1 | 9/2014 | Rezach | |
| 2014/0358182 A1 | 12/2014 | Puekert | |
| 2015/0134004 A1 * | 5/2015 | Ziolo | A61B 17/7032 606/266 |
| 2015/0182258 A1 * | 7/2015 | Jackson | A61B 17/7028 606/257 |
| 2016/0066958 A1 | 3/2016 | Raju et al. | |
| 2018/0153600 A1 * | 6/2018 | Koller | A61B 17/8625 |

* cited by examiner

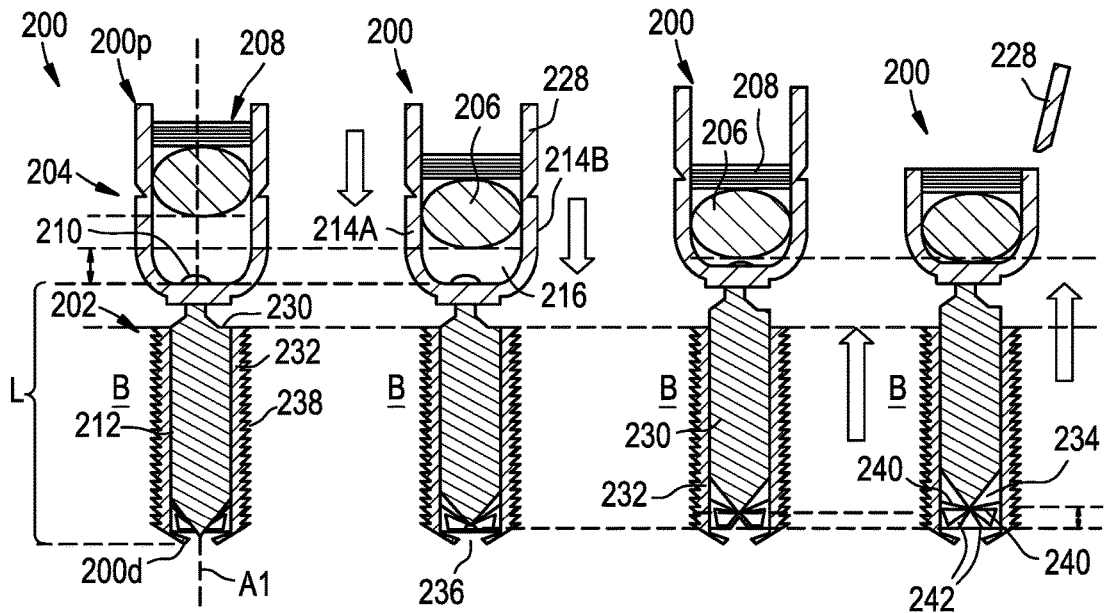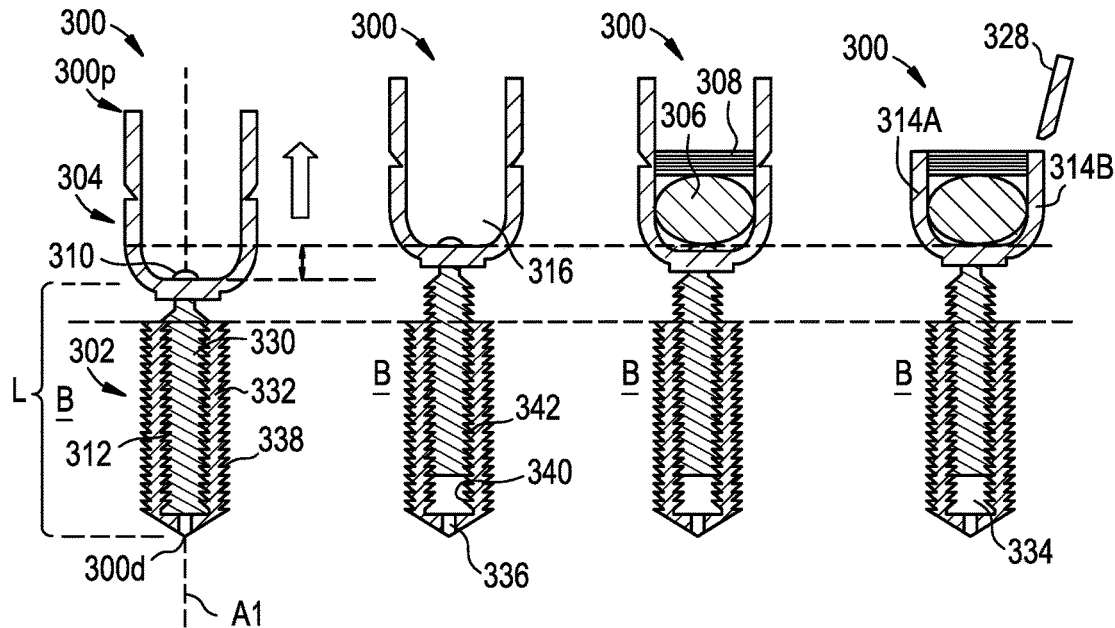

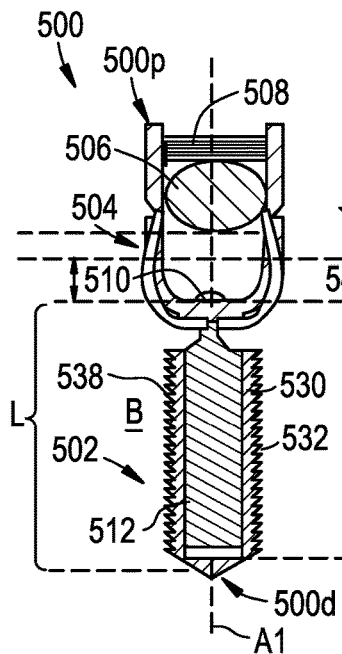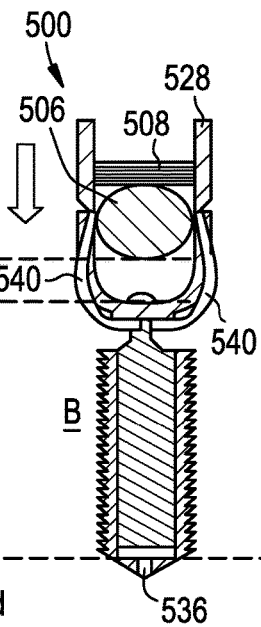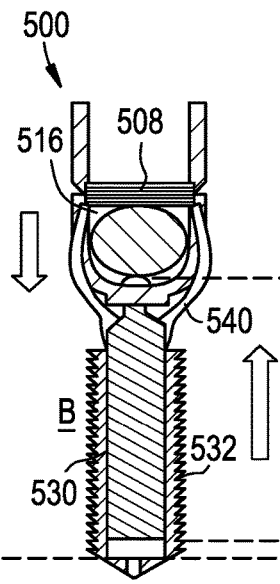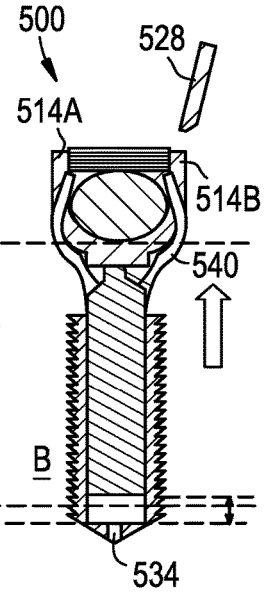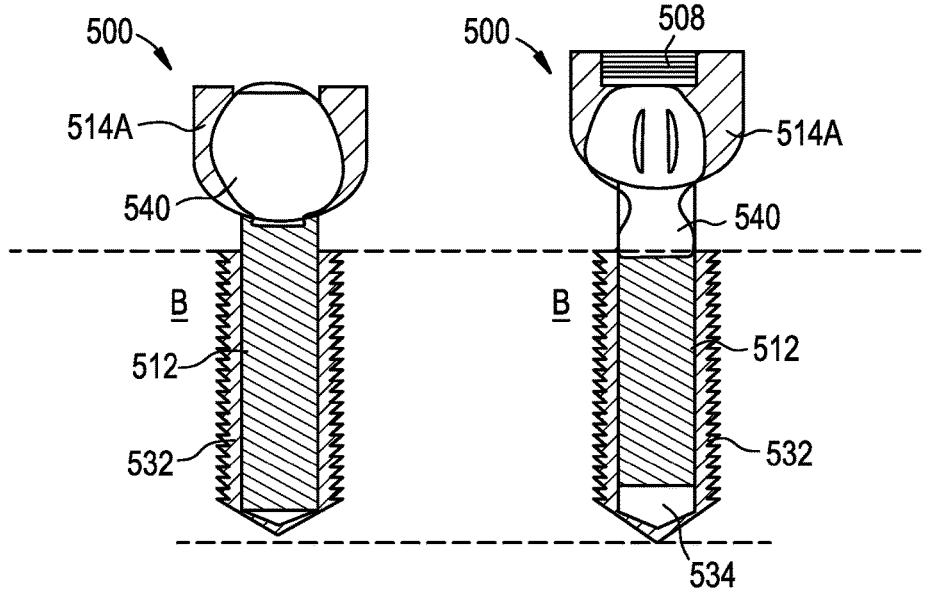

LONGITUDINALLY-ADJUSTABLE BONE ANCHORS AND RELATED METHODS

FIELD

Longitudinally-adjustable bone anchors and related methods are disclosed herein.

BACKGROUND

Fixation systems can be used in orthopedic surgery to maintain a desired spatial relationship between multiple bones or bone fragments. For example, various conditions of the spine, such as fractures, deformities, and degenerative disorders, can be treated by attaching a spinal fixation system to one or more vertebrae. Such systems typically include a spinal fixation element, such as a rigid or flexible rod or plate, that is coupled to the vertebrae by attaching the element to various anchoring devices, such as screws, hooks, or wires. Once installed, the fixation system holds the vertebrae in a desired position until healing or spinal fusion can occur, or for some other period of time.

Placing the fixation system typically requires that one or more rods be bent or contoured very accurately to fit within several bone anchors implanted along the spine. The rods are typically bent in three dimensions and may need to be bent to match adjacent rods that are working in concert, to accommodate a deformity, or to account for gravity and soft tissue forces. In addition, contouring a rod too many times can reduce the fatigue life of the rod. In view of these and other challenges, the precise contouring of a rod to approximate the rod to a series of bone anchors is a time consuming and artful procedure.

It can also be a very important procedure. The alignment of a patient's vertebrae is usually a key output of the surgery and the patient's wellbeing can depend on post-operative alignment. The rods apply the corrective loads to the spine and are what hold the alignment post-surgery while healing or fusion takes place. If the rods are not contoured accurately, too much pre-stress can be applied to the bone anchors, which can result in mal-union or mal-alignment. For example, when a rod is improperly contoured, significant reduction forces must typically be applied to bring the rod into alignment with the bone anchors. These forces can cause unequal loading or loosening of the bone anchors at the anchor-bone interface, which can result in instrument or construct failure, non-union, or pain. As shown in FIG. 1A, application of significant reduction forces, e.g., using a reduction instrument of the type shown in FIG. 1B, to bone anchors at intermediate levels of a fixation construct can cause damage to the osseous threads and loosening or dislocation of the bone anchors. A similar phenomenon can occur at the end levels of the construct. For example, performing a cantilever rod reduction maneuver to restore lordosis (as shown in FIG. 1C) can result in significant reduction and recoil forces at the screw-bone interfaces (as shown in FIG. 1D), which ultimately can lead to failure at the anchor-bone interface with loosening or dislocation of the bone anchor (as shown in FIG. 1E).

Application of significant reduction forces can also cause iatrogenic central or foraminal stenosis by segmental translation of one vertebra in relation to another. For example, as shown in FIGS. 1F-1G, rod-to-anchor reduction can cause sagittal plane translation of one vertebra (e.g., C4 as shown) relative to an adjacent vertebra (e.g., C5 as shown), pinching the nerve tissue and resulting in pain, weakness, numbness, loss of function, or other symptoms.

Some surgeons may try to limit the reduction forces by backing out the bone anchor a few turns to meet the rod, however this can have the same effect of compromising bone purchase and weakening the anchor-bone interface.

SUMMARY

Longitudinally-adjustable bone anchors and related methods are disclosed herein. The ability to adjust a bone anchor longitudinally can allow the surgeon to bring an implanted bone anchor up to the rod instead of or in addition to bringing the rod down to the bone anchor, which can simplify or eliminate the rod contouring step and reduce or eliminate reduction forces. For example, the surgeon can use a pre-bent rod or put "ideal contours" into a rod, lay the rod across a series of bone anchors, and adjust each bone anchor longitudinally to meet the rod. As another example, coarse adjustment of the fixation system can be achieved by contouring the rod and then fine adjustments can be made by bringing each bone anchor up or down to the rod. Various adjustment mechanisms are disclosed, including bone anchors with telescoping portions and bone anchors with risers or spacers.

In some embodiments, a longitudinally-adjustable bone anchor includes a receiver member that defines a rod-receiving recess; and a shank having inner and outer telescoping portions, the outer telescoping portion of the shank including a bone-engaging thread and defining an inner cavity, the inner telescoping portion including a shaft disposed in the cavity of the outer telescoping portion and a head that movably couples the shank to the receiver member; wherein the inner and outer telescoping portions are longitudinally-adjustable relative to one another to adjust a length of the bone anchor.

The inner telescoping portion can be constrained from rotating axially relative to the outer telescoping portion. The inner telescoping portion can be threaded into the cavity of the outer telescoping portion. The bone anchor can include a locking element configured to selectively prevent distal movement of the inner telescoping portion relative to the outer telescoping portion, to prevent proximal movement of the inner telescoping portion relative to the outer telescoping portion, or to prevent both proximal and distal movement of the inner telescoping portion relative to the outer telescoping portion. The locking element can include one or more biased teeth configured to project radially inward from an inner sidewall of the cavity to engage the shaft as the shaft is moved proximally within the cavity. The locking element can include a threaded engagement between the inner and outer telescoping portions. The locking element can include a locking ring disposed around the shaft of the inner telescoping portion and configured to engage ratchet teeth spaced longitudinally along an inner surface of the cavity. The cavity can include proximal and distal portions separated by an annular projection. The shaft can be biased distally relative to the outer telescoping portion by a spring disposed between the annular projection and a shoulder formed on the shaft. The locking element can include one or more tabs extending from the receiver member. The tabs can be configured to wedge between the inner and outer telescoping portions when a distally-directed force is applied to the tabs. Tightening a closure mechanism to the receiver member can apply a distally-directed force to the tabs. Each of the tabs can have a folded position and a deployed position, the tabs in the deployed position being configured to contact the outer telescoping portion and support the receiver member in an elevated position relative to the outer telescoping portion.

In some embodiments, a longitudinally-adjustable bone anchor includes a receiver member that defines a rod-receiving channel having a first rod seat; a threaded shank movably coupled to the receiver member; and a spacer disposed in the rod-receiving channel of the receiver member and having a distal surface that contacts the first rod seat and a proximal surface that defines a second rod seat spaced a distance apart from the first rod seat.

The first rod seat can be defined by opposed U-shaped recesses formed in the receiver member. The distal surface of the spacer can be a section of a cylinder. The proximal surface of the spacer can be a section of a cylinder. The spacer can include one or more protrusions that engage an outer sidewall of the receiver member to prevent translation of the spacer relative to the receiver member along a longitudinal axis of the spacer. The protrusions can extend from the distal surface of the spacer. The protrusions can be convexly curved. The protrusions can include inwardly-facing planar surfaces that engage corresponding outwardly-facing planar surfaces of the receiver member. The spacer can include opposed planar sidewalls connecting the proximal and distal surfaces of the spacer that engage respective opposed planar sidewalls of the rod-receiving channel.

In some embodiments, a bone fixation method includes implanting a bone anchor in a bone of a patient, the bone anchor having a proximal portion that includes a rod seat configured to receive a fixation rod therein and a distal portion configured to engage bone, the bone anchor having a length L defined between the rod seat and a distal-most tip of the bone anchor; positioning a fixation rod with respect to the bone anchor such that the fixation rod is offset proximally from the rod seat; and extending the length L of the bone anchor to reduce the offset between the fixation rod and the rod seat.

In some embodiments, the length L is adjusted independently of adjusting a position of the distal portion of the bone anchor relative to the bone. In some embodiments, the distal portion of the bone anchor includes a thread that is threaded into the bone and the length L is adjusted without moving the thread relative to the bone. In some embodiments, the length L is adjusted independently of adjusting an angle between the proximal and distal portions of the bone anchor. In some embodiments, the length L is adjusted at a location other than an interface between the proximal and distal portions of the bone anchor. The distal portion of the bone anchor can include inner and outer telescoping portions and adjusting the length L can include moving the inner telescoping portion proximally relative to the outer telescoping portion. The method can include locking at least one of proximal movement, distal movement, and both proximal and distal movement of the inner telescoping portion relative to the outer telescoping portion via a locking element. The locking element can include at least one of: biased teeth configured to deploy from a cavity of the outer telescoping portion to engage the inner telescoping portion; a threaded engagement between the inner and outer telescoping portions; a locking ring disposed around the inner telescoping portion and engaged with ratchet teeth formed in a cavity of the outer telescoping portion; tabs configured to wedge between the inner and outer telescoping portions when a distally-directed force is applied to the tabs; and tabs having a folded position and a deployed position, the tabs in the deployed position being configured to contact the outer telescoping portion and support the proximal portion of the bone anchor in an elevated position relative to the outer telescoping portion. Adjusting the length L can include inserting a spacer between the rod and the proximal portion of the receiver member, the rod seat being defined by a proximal surface of the spacer. The method can include selecting the spacer from a kit of a plurality of spacers, each of the plurality of spacers having a different height and the selected spacer having a height corresponding to a desired degree of extension of the length L.

BRIEF DESCRIPTION OF THE DRAWINGS

FIG. 2A is a sectional schematic side view of a longitudinally-adjustable bone anchor and a spinal rod, shown before rod reduction;

FIG. 2B is another sectional schematic side view of the bone anchor of FIG. 2A, shown at an intermediate stage of rod reduction;

FIG. 2C is another sectional schematic side view of the bone anchor of FIG. 2A, shown in a longitudinally-adjusted configuration;

FIG. 2D is another sectional schematic side view of the bone anchor of FIG. 2A, shown in a final configuration;

FIG. 3A is a sectional schematic side view of a longitudinally-adjustable bone anchor;

FIG. 3B is another sectional schematic side view of the bone anchor of FIG. 3A, shown in a longitudinally-adjusted configuration;

FIG. 3C is another sectional schematic side view of the bone anchor of FIG. 3A, shown with a spinal rod seated in the bone anchor;

FIG. 3D is another sectional schematic side view of the bone anchor of FIG. 3A, shown in a final configuration;

FIG. 5A is a sectional schematic side view of a longitudinally-adjustable bone anchor and a spinal rod, shown before rod reduction;

FIG. 5B is another sectional schematic side view of the bone anchor of FIG. 5A, shown at an intermediate stage of rod reduction;

FIG. 5C is another sectional schematic side view of the bone anchor of FIG. 5A, shown in a longitudinally-adjusted configuration;

FIG. 5D is another sectional schematic side view of the bone anchor of FIG. 5A, shown in a final configuration;

FIG. 5E is another sectional schematic side view of the bone anchor of FIG. 5A, shown before longitudinal adjustment;

FIG. 5F is another sectional schematic side view of the bone anchor of FIG. 5A, shown after longitudinal adjustment;

DETAILED DESCRIPTION

Longitudinally-adjustable bone anchors and related methods are disclosed herein. The ability to adjust a bone anchor longitudinally can allow the surgeon to bring an implanted bone anchor up to the rod instead of or in addition to bringing the rod down to the bone anchor, which can simplify or eliminate the rod contouring step and reduce or eliminate reduction forces. For example, the surgeon can use a pre-bent rod or put "ideal contours" into a rod, lay the rod across a series of bone anchors, and adjust each bone anchor longitudinally to meet the rod. As another example, coarse adjustment of the fixation system can be achieved by contouring the rod and then fine adjustments can be made by bringing each bone anchor up or down to the rod. Various adjustment mechanisms are disclosed, including bone anchors with telescoping portions and bone anchors with risers or spacers.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments. The features illustrated or described in connection with one exemplary embodiment may be combined with the features of other embodiments.

Prior Art Bone Anchor

Figure 1A:
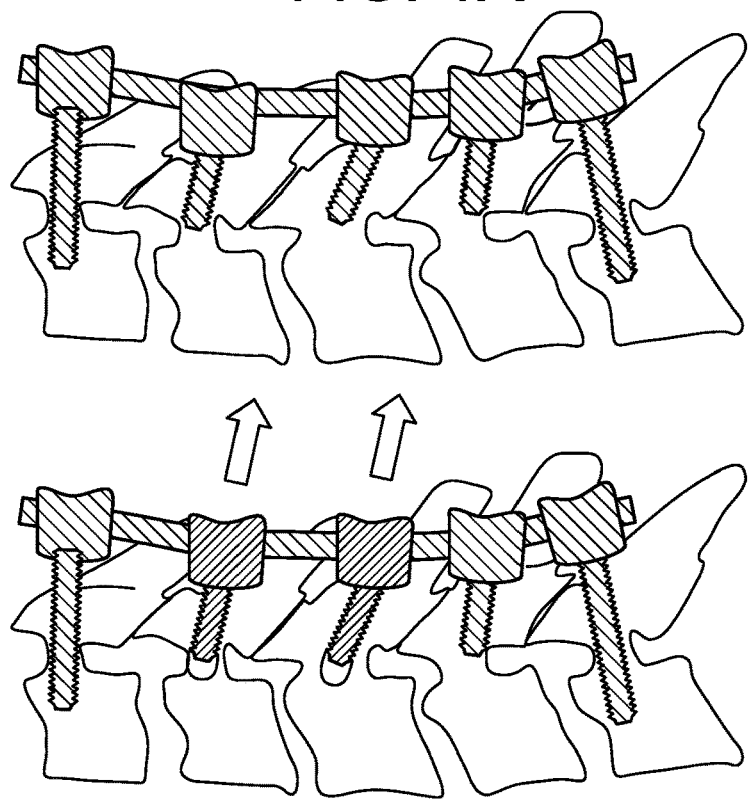
FIG. 1A is a sectional schematic view of a human spine instrumented with a fixation construct, showing dislocation of intermediate level bone anchors.
Figure 1B:
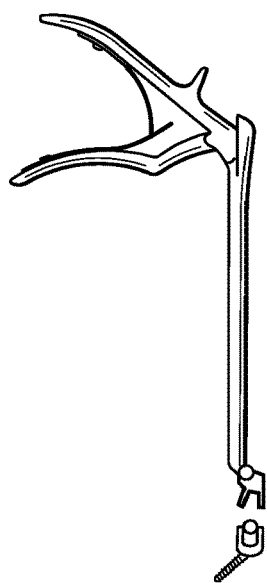
FIG. 1B is a side view of a reduction instrument, a spinal rod, and a bone anchor.
Figure 1C:
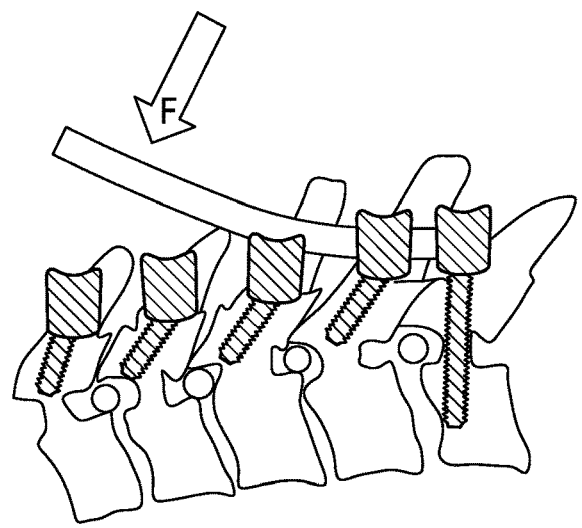
FIG. 1C is a sectional schematic view of a human spine instrumented with a fixation construct, showing a cantilever rod reduction maneuver.
Figure 1D:
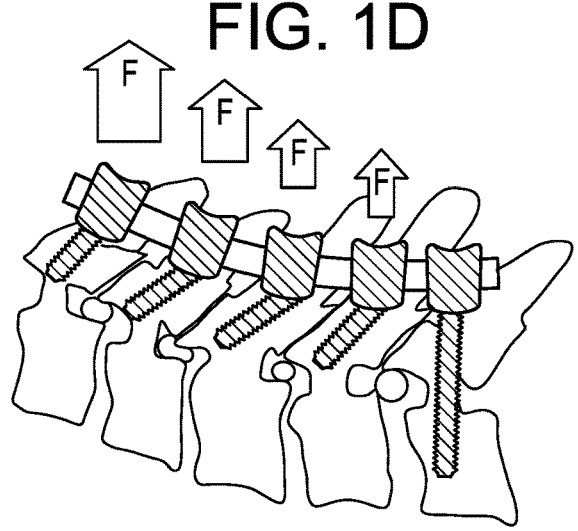
FIG. 1D is a sectional schematic view of the human spine and fixation construct of FIG. 1C, showing reduction and recoil forces at the screw-bone interfaces.
Figure 1E:
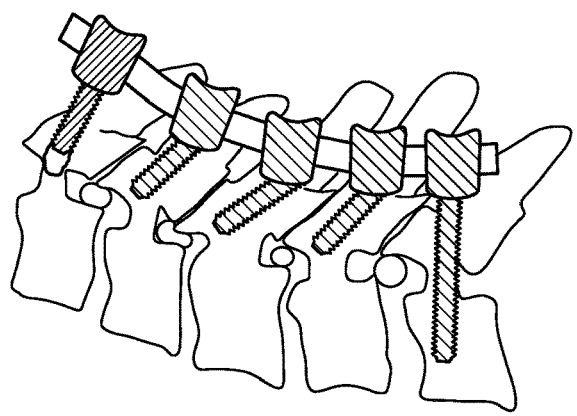
FIG. 1E is a sectional schematic view of the human spine and fixation construct of FIG. 1C, showing dislocation of an end level bone anchor.
Figure 1F:
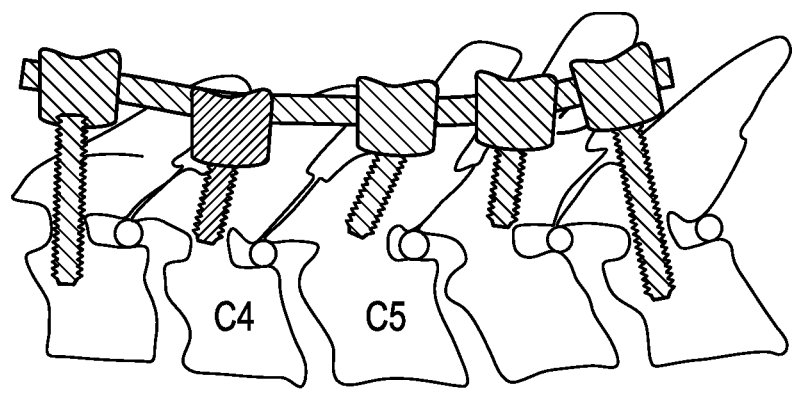
FIG. 1F is a sectional schematic view of a human spine instrumented with a fixation construct, before reducing a rod into an intermediate bone anchor.
Figure 1G:
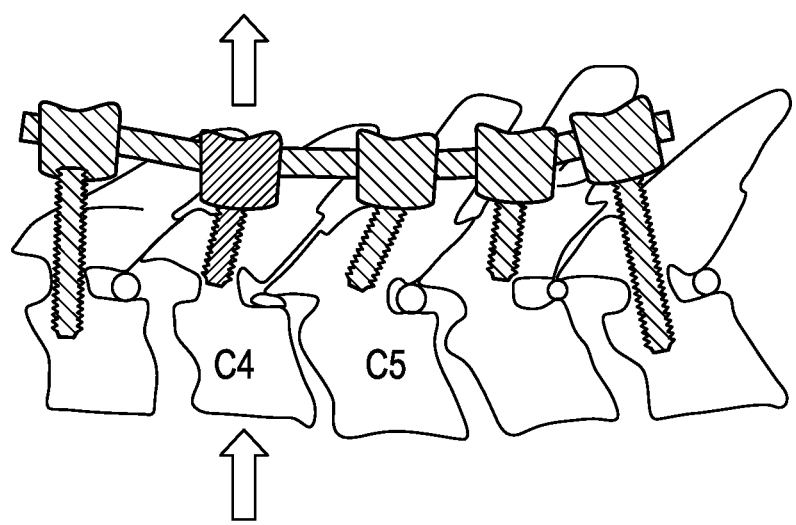
FIG. 1G is a sectional schematic view of the human spine and fixation construct of FIG. 1F, after reducing the rod into the intermediate bone anchor, showing stenosis caused by said reduction.
Figure 1H:
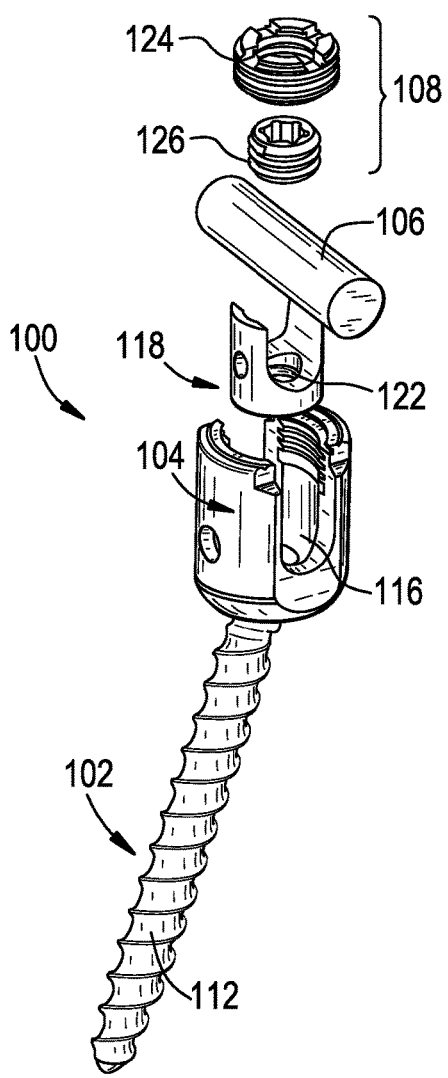
FIG. 1H is an exploded perspective view of a prior art bone anchor.
Figure 1I:
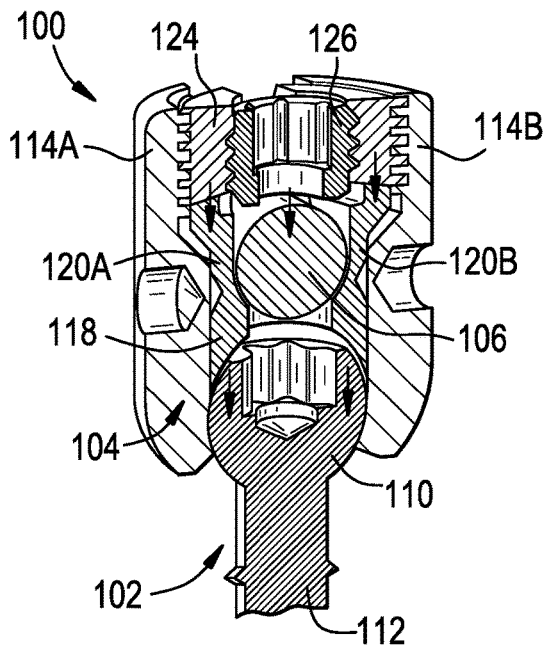
FIG. 1I is a sectional perspective view of the bone anchor of FIG. 1H.
Figure 1J:
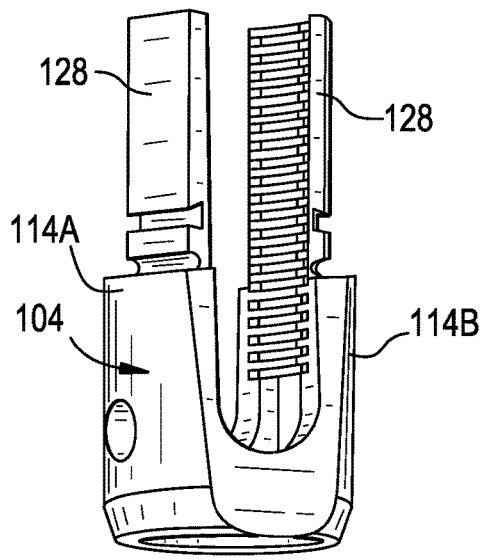
FIG. 1J is a perspective view of a receiver member of the bone anchor of FIG. 1H, shown with reduction tabs.

FIGS. 1H-1J illustrate a prior art bone anchor 100 with various features that can be included in the bone anchors 200, 300, 400, 500, 600 described below. It will be appreciated that the illustrated bone anchor 100 is exemplary and that the bone anchors 200, 300, 400, 500, 600 described below can include additional or alternative features.

The illustrated bone anchor 100 includes an anchor portion or shank 102, a head or receiver member 104 for receiving a spinal fixation element, such as a spinal rod 106, to be coupled to the anchor portion 102, and a fastener or closure mechanism 108 to capture a spinal fixation element within the receiver member and fix the spinal fixation element with respect to the receiver member. The anchor portion 102 includes a proximal head 110 and a distal shaft 112 configured to engage bone. The receiver member 104 has a proximal end having a pair of spaced apart arms 114A, 114B defining a recess or channel 116 therebetween and a distal end having a distal end surface defining an opening through which at least a portion of the anchor portion 102 extends. The closure mechanism 108 can be positionable between and can engage the arms 114A, 114B to capture a spinal fixation element, e.g., a spinal rod 106, within the receiver member 104 and fix the spinal fixation element with respect to the receiver member.

The proximal head 110 of the anchor portion 102 is generally in the shape of a truncated sphere having a planar proximal surface and an approximately spherically-shaped distal surface. The illustrated bone anchor 100 is a polyaxial bone screw designed for posterior implantation in the pedicle or lateral mass of a vertebra. The proximal head 110 of the anchor portion 102 engages the distal end of the receiver member 104 in a ball and socket like arrangement in which the proximal head and the distal shaft 112 can pivot relative to the receiver member. The distal surface of the proximal head 110 of the anchor portion 102 and a mating surface within the distal end of the receiver member 104 can have any shape that facilitates this arrangement, including, for example, spherical (as illustrated), toroidal, conical, frustoconical, and any combinations of these shapes.

The distal shaft 112 of the anchor portion 102 can be configured to engage bone and, in the illustrated embodiment, includes an external bone engaging thread. The thread form for the distal shaft 112, including the number of threads, the pitch, the major and minor diameters, and the thread shape, can be selected to facilitate connection with bone. Exemplary thread forms are disclosed in U.S. Patent Application Publication No. 2011/0288599, filed on May 18, 2011, and in U.S. Patent Application Publication No. 2013/0053901, filed on Aug. 22, 2012, both of which are hereby incorporated by reference herein. The distal shaft 112 can also include other structures for engaging bone, including a hook. The distal shaft 112 of the anchor portion 102 can be cannulated, having a central passage or cannula extending the length of the anchor portion to facilitate delivery of the anchor portion over a guidewire in, for example, minimally-invasive procedures. Other components of the bone anchor 100, including, for example, the closure mechanism 108, the receiver member 104, and the compression member or cap 118 (discussed below) can be cannulated or otherwise have an opening to permit delivery over a guidewire. The distal shaft 112 can also include one or more sidewall openings or fenestrations that communicate with the cannula to permit bone in-growth or to permit the dispensing of bone cement or other materials through the anchor portion 102. The sidewall openings can extend radially from the cannula through the sidewall of the distal shaft 112. Exemplary systems for delivering bone cement to the bone anchor 100 and alternative bone anchor configurations for facilitating cement delivery are described in U.S. Patent Application Publication No. 2010/0114174, filed on Oct. 29, 2009, which is hereby incorporated by reference herein. The distal shaft 112 of the anchor portion 102 can also be coated with materials to permit bone growth, such as, for example, hydroxyapatite, and the bone anchor 100 can be coated partially or entirely with anti-infective materials, such as, for example, tryclosan.

The proximal end of the receiver member 104 includes a pair of spaced apart arms 114A, 114B defining a U-shaped recess 116 therebetween for receiving a spinal fixation element, e.g., a spinal rod 106. Each of the arms 114A, 114B can extend from the distal end of the receiver member 104 to a free end. The outer surfaces of each of the arms 114A, 114B can include a feature, such as a recess, dimple, notch, projection, or the like, to facilitate connection of the receiver member 104 to instruments. For example, the outer surface of each arm 114A, 114B can include an arcuate groove at the respective free end of the arms. Such grooves are described in more detail in U.S. Pat. No. 7,179,261, issued on Feb. 20, 2007, which is hereby incorporated by reference herein.

The distal end of the receiver member 104 includes a distal end surface which is generally annular in shape defining a circular opening through which at least a portion of the anchor portion 102 extends. For example, the distal shaft 112 of the anchor portion 102 can extend through the opening.

The anchor portion 102 can be selectively fixed relative to the receiver member 104. Prior to fixation, the anchor portion 102 is movable relative to the receiver member 104 within a cone of angulation generally defined by the geometry of the distal end of the receiver member and the proximal head 110 of the anchor portion 102. The bone anchor 100 can be a favored angle screw, for example as disclosed in U.S. Pat. No. 6,974,460, issued on Dec. 13, 2005, and in U.S. Pat. No. 6,736,820, issued on May 18, 2004, both of which are hereby incorporated by reference herein. Alternatively, the bone anchor 100 can be a conventional (non-biased) polyaxial screw in which the anchor portion 102 pivots in the same amount in every direction.

The spinal fixation element, e.g., the spinal rod 106, can either directly contact the proximal head 110 of the anchor portion 102 or can contact an intermediate element, e.g., a compression member 118. The compression member 118 can be positioned within the receiver member 104 and interposed between the spinal rod 106 and the proximal head 110 of the anchor portion 102 to compress the distal outer surface of the proximal head into direct, fixed engagement with the distal inner surface of the receiver member 104. The compression member 118 can include a pair of spaced apart arms 120A and 120B defining a U-shaped seat 122 for receiving the spinal rod 106 and a distal surface for engaging the proximal head 110 of the anchor portion 102.

The proximal end of the receiver member 104 can be configured to receive a closure mechanism 108 positionable between and engaging the arms 114A, 114B of the receiver member. The closure mechanism 108 can be configured to capture a spinal fixation element, e.g., a spinal rod 106, within the receiver member 104, to fix the spinal rod relative to the receiver member, and to fix the anchor portion 102 relative to the receiver member. The closure mechanism 108 can be a single set screw having an outer thread for engaging an inner thread provided on the arms 114A, 114B of the receiver member 104. In the illustrated embodiment, however, the closure mechanism 108 includes an outer set screw 124 operable to act on the compression member 118 and an inner set screw 126 operable to act on the rod 106. Various other closure mechanisms 108 can be used instead or in addition, such as a nut that extends around an outer circumference of the receiver member 104, a cap or fastener that slides onto the receiver member from the side, or a cap or fastener that locks to the receiver member by quarter-turn rotation. The receiver member 104 can include, can be formed integrally with, or can be coupled to one or more extension tabs 128 (shown in FIG. 1J) that extend proximally from the receiver member 104 to functionally extend the length of the arms 114A, 114B. The extension tabs 128 can facilitate installation and assembly of a fixation or stabilization construct and can be removed prior to completing a surgical procedure.

The bone anchor 100 can be used with a spinal fixation element such as rigid spinal rod 106. Alternatively, the spinal fixation element can be a dynamic stabilization member that allows controlled mobility between the instrumented vertebrae.

In use, the bone anchor 100 can be assembled such that the distal shaft 112 extends through the opening in the distal end of the receiver member 104 and the proximal head 110 of the anchor portion 102 is received in the distal end of the receiver member 104. A driver instrument can be fitted with the anchor portion 102 to drive the anchor portion into bone. The compression member 118 can be positioned within the receiver member 104 such that the arms 120A, 120B of the compression member are aligned with the arms 114A, 114B of the receiver member 104 and the lower surface of the compression member 118 is in contact with the proximal head 110 of the anchor portion 102. A spinal fixation element, e.g., the spinal rod 106, can be located in the recess 116 of the receiver member 104. The closure mechanism 108 can be engaged with the inner thread provided on the arms 114A, 114B of the receiver member 104. A torsional force can be applied to the outer set screw 124 to move it within the recess 116 so as to force the compression member 118 onto the proximal head 110 of the anchor portion 102, thereby locking the angular position of the anchor portion 102 relative to the receiver member 104. A torsional force can be applied to the inner set screw 126 to force the spinal rod 106 into engagement with the compression member 118 and thereby fix the spinal rod 106 relative to the receiver member 104.

The bone anchors 200, 300, 400, 500, 600 described below can be configured to operate in conjunction with, or can include any of the features of, bone anchors of the type described above or other types known in the art. Exemplary bone anchors include monoaxial screws, polyaxial screws, uniplanar screws, favored-angle screws, and/or any of a variety of other bone anchor types known in the art.

Longitudinally-Adjustable Bone Anchors

FIGS. 2A-2D illustrate an exemplary embodiment of a longitudinally-adjustable bone anchor 200. The bone anchor 200 can include a proximal end 200p and a distal end 200d that define a proximal-distal or longitudinal axis A1 extending therebetween. The bone anchor 200 can be longitudinally-adjustable or expandable such that a length L of the bone anchor, defined between a distal-most tip of the bone anchor and a proximal rod seat of the bone anchor, can be modified. The bone anchor 200 can be adjustable in situ, e.g., after implanting in bone, or prior to being implanted.

The bone anchor 200 can include an anchor portion or shank 202, a head or receiver member 204, and a closure mechanism 208.

The shank 202 can include inner and outer telescoping portions 230, 232 movable with respect to one another to adjust the length L of the bone anchor 200. In the illustrated embodiment, the outer telescoping portion 232 includes a sleeve that defines an inner cavity 234. The cavity 234 can be sized to receive at least a portion of the inner telescoping portion 230 therein. The cavity 234 can include a closed or substantially-closed distal end and an open proximal end. The sleeve 232 can include a cannulation 236 that extends from the cavity 234 to the distal tip of the sleeve, e.g., to allow the sleeve to be delivered over a guidewire or to allow a flowable material to be delivered through a distal tip of the sleeve and into surrounding bone. An outer surface of the sleeve 232 can include a bone-engaging thread 238.

The inner telescoping portion 230 can include a distal shaft 212 mounted in the cavity 234 of the sleeve 232 and a proximal head 210 to which the receiver member 204 can be coupled. The distal shaft 212 can be slidably disposed within the cavity 234 to allow the distal shaft to translate longitudinally with respect to the sleeve 232. The distal shaft 212 can be free to rotate about the axis A1 relative to the sleeve 232, or rotation between the shaft and the sleeve can be limited or completely restricted. Various features for restricting rotation can be used. For example, the sleeve 232 can include a transverse pin or a ridge that is received in a slot or groove formed in the shaft 212 to allow the shaft to translate longitudinally relative to the sleeve but to prevent the shaft from rotating relative to the sleeve. In other arrangements, the pin or ridge can be included in the inner shaft 212 and the slot or groove can be formed in the outer sleeve 232. The shaft 212 can include a cannulation that extends longitudinally therethrough, e.g., to allow the shaft to be delivered over a guidewire or to allow a flowable material to be delivered through the shaft and into the cavity 234 or into bone in which the bone anchor 200 is implanted.

The bone anchor 200 can include one or more stops configured to limit the degree to which the shaft 212 can translate longitudinally relative to the sleeve 232. For example, the bone anchor 200 can include a shoulder, pin, or other feature at a proximal end of the sleeve 232 to prevent the shaft 212 from being removed proximally from the sleeve during use.

The bone anchor 200 can include a locking element configured to selectively lock longitudinal movement between the shaft 212 and the sleeve 232. The locking element can be configured to prevent distal movement of the shaft 212 relative to the sleeve 232, to prevent proximal movement of the shaft relative to the sleeve, or to prevent both distal and proximal movement of the shaft relative to the sleeve.

In the illustrated embodiment, the locking element includes one or more biased teeth 240 configured to project radially inward from the inner sidewall of the cavity 234 to support the shaft 212 and prevent or resist distal movement of the shaft relative to the sleeve 232. The teeth 240 can be attached to the sidewall of the cavity 234, for example via a living hinge or other joint. The teeth 240 can be biased in a radially-inward direction. Accordingly, the shaft 212 can initially hold the teeth 240 in a retracted position and then, as the shaft is lifted proximally relative to the sleeve 232, the teeth can deploy into the cavity 234. The teeth 240 can be biased by respective leaf springs 242 as shown, by resilient or shape-memory material properties of the teeth, or by any of a variety of other bias mechanisms, such as coil springs and the like. In the illustrated embodiment, the teeth 240 are deployed to engage a distal-facing surface of the shaft 212 and prevent or resist distal movement of the shaft. In other arrangements, the teeth 240 can be deployed into recesses formed in the sidewall of the shaft 212 to prevent or resist both proximal and distal movement, or can grip an outer surface of the shaft 212 with sufficient strength to prevent or resist both proximal and distal movement. The teeth 240 can define unidirectional ramping surfaces, such that the teeth prevent distal movement but allow proximal movement or vice-versa.

While biased teeth 240 are shown, it will be appreciated that various other locking elements can be used instead or in addition. For example, a flowable material can be delivered through a cannulation of the shaft 212 to fill the void space left in the cavity 234 once the shaft is translated proximally relative to the sleeve 232. The flowable material can be a curable material configured to solidify within the cavity 234 to lock movement between the shaft 212 and the sleeve 232. Exemplary materials include cements, adhesives, and the like. As another example, the sleeve 232 can include one or more spring-loaded pins configured to deploy into the cavity 234 as the shaft 212 is translated proximally relative to the sleeve. In some embodiments, a plurality of pins can be spaced longitudinally along the inner surface of the sleeve 232 to provide incremental locking at a plurality of discrete points along the length of the sleeve. As yet another example, teeth, pins, hooks, barbs, or other structures can be deployed from the shaft 212 to engage the sleeve 232 to lock movement therebetween. Such structures can be biased radially outward from the shaft 212. Alternatively, or in addition, such structures can be deployed from the shaft 212 by inserting an elongated rod through a cannulation of the shaft to push the structures out into engagement with the sleeve 232.

The shank 202, receiver member 204, and closure mechanism 208 can include any of the features of the corresponding components of the bone anchor 100 described above. For example, as shown, the receiver member 204 can be polyaxially coupled to the head 210 of the shank 202 and can include a pair of spaced apart arms 214A, 214B defining a recess 216 therebetween. The closure mechanism 208 can be positionable between and can engage the arms 214A, 214B to capture a spinal fixation element, e.g., a spinal rod 206, within the receiver member 204, to fix the spinal fixation element with respect to the receiver member, and to fix the receiver member with respect to the shank 202.

In use, the bone anchor 200 can be initially configured such that the inner telescoping portion 230 is disposed in a distal position with respect to the outer telescoping portion 232, as shown in FIG. 2A. In the initial configuration, the locking element (e.g., the deployable teeth 240) can be in a retracted or disengaged position. A driver instrument can be applied to the head 210 of the anchor portion 202 to rotate the anchor portion about the axis A1. The inner and outer telescoping portions 230, 232 can be rotationally fixed to one another at least in the initial configuration such that torque applied to the inner telescoping portion is in turn applied to the outer telescoping portion to drive the anchor portion 202 into bone B.

Once the anchor portion 202 is driven to the target depth, or at any other desired time, a spinal rod 206 can be positioned in the receiver member 204 and the closure mechanism 208 can be applied to secure the rod, as shown in FIG. 2B. In the illustrated embodiment, a set screw 208 is threaded into extension tabs 228 that extend proximally from the arms 214A, 214B of the receiver member 204.

As the set screw 208 is tightened to reduce the rod 206 into the receiver member 204, as shown in FIG. 2C, the inner telescoping portion 230 can be pulled proximally such that it translates longitudinally with respect to the outer telescoping portion 232 while the outer telescoping portion remains at a fixed longitudinal position with respect to the surrounding bone B. The set screw 208 can be advanced distally within the receiver member 204 until the rod 206 is securely fastened to the bone anchor 200, as shown in FIG. 2D, and the reduction tabs 228 can be removed.

At any point in the above process, the locking element can be deployed or engaged to lock the relative longitudinal positions of the inner and outer telescoping portions 230, 232. The bone anchor 200 can allow the length L of the bone anchor to be adjusted independently of adjusting an angle between the receiver member 204 and the shank 202. The bone anchor 200 can allow the length L of the bone anchor to be adjusted at a location other than the interface between the receiver member 204 and the shank 202. The bone anchor 200 can allow the length L of the bone anchor to be adjusted, and/or can allow the rod to be moved towards the receiver member, without disturbing the anchor-bone interface, e.g., without moving the thread 238 relative to the bone.

It will thus be appreciated that the above process allows the length L of the bone anchor 200 to be adjusted in situ such that the receiver member 204 can be pulled proximally towards the rod 206 instead of or in addition to forcing the rod distally towards the receiver member. By reducing or eliminating the need to reduce the rod 206 distally relative to the anchor portion 202, reduction forces applied to the anchor-bone interface can be reduced, thereby improving the strength and stability of the implanted construct. This can also reduce or eliminate the need to precisely contour the rod 206 to the bone anchor 200, simplifying the surgical procedure.

FIGS. 3A-3D illustrate an exemplary embodiment of a longitudinally-adjustable bone anchor 300. The bone anchor 300 can include a proximal end 300p and a distal end 300d that define a proximal-distal or longitudinal axis A1 extending therebetween. The bone anchor 300 can be longitudinally-adjustable or expandable such that a length L of the bone anchor, defined between a distal-most tip of the bone anchor and a proximal rod seat of the bone anchor, can be modified. The bone anchor 300 can be adjustable in situ, e.g., after implanting in bone, or prior to being implanted.

The bone anchor 300 can include an anchor portion or shank 302, a head or receiver member 304, and a closure mechanism 308.

The shank 302 can include inner and outer telescoping portions 330, 332 movable with respect to one another to adjust the length L of the bone anchor 300. In the illustrated embodiment, the outer telescoping portion 332 includes a sleeve that defines an inner cavity 334. The cavity 334 can be sized to receive at least a portion of the inner telescoping portion 330 therein. The cavity 334 can include a closed or substantially-closed distal end and an open proximal end. The sleeve 332 can include a cannulation 336 that extends from the cavity 334 to the distal tip of the sleeve, e.g., to allow the sleeve to be delivered over a guidewire or to allow a flowable material to be delivered through a distal tip of the sleeve and into surrounding bone. An outer surface of the sleeve 332 can include a bone-engaging thread 338 and an inner surface of the sleeve can include a thread 340 for engaging the inner telescoping portion 330.

The inner telescoping portion 330 can include a distal shaft 312 mounted in the cavity 334 of the sleeve 332 and a proximal head 310 to which the receiver member 304 can be coupled. The distal shaft 312 can include an outer thread 342 engaged with the inner thread 340 of the sleeve 332 to allow the distal shaft to translate longitudinally with respect to the sleeve by rotating the shaft within the cavity 334 about the axis A1. The shaft 312 can include a cannulation that extends longitudinally therethrough, e.g., to allow the shaft to be delivered over a guidewire or to allow a flowable material to be delivered through the shaft and into the cavity 334 or into bone in which the bone anchor 300 is implanted.

The bone anchor 300 can include one or more stops configured to limit the degree to which the shaft 312 can translate longitudinally relative to the sleeve 332. For example, the bone anchor 300 can include a shoulder, pin, or other feature at a proximal end of the sleeve 332 to prevent the shaft 312 from being removed proximally from the sleeve during use.

The bone anchor 300 can include a locking element configured to selectively lock longitudinal movement between the shaft 312 and the sleeve 332. The locking element can be configured to prevent distal movement of the shaft 312 relative to the sleeve 332, to prevent proximal movement of the shaft relative to the sleeve, or to prevent both distal and proximal movement of the shaft relative to the sleeve.

In the illustrated embodiment, the locking element is formed by the threaded interface between the shaft 312 and the outer sleeve 332. It will be appreciated, however, that other locking elements can be used instead or in addition. For example, a flowable material can be delivered through a cannulation of the shaft 312 to fill the void space left in the cavity 334 once the shaft is translated proximally relative to the sleeve 332. The flowable material can be a curable material configured to solidify within the cavity 334 to lock movement between the shaft 312 and the sleeve 332. Exemplary materials include cements, adhesives, and the like. As another example, the sleeve 332 can include one or more spring-loaded pins configured to deploy into the cavity 334 as the shaft 312 is translated proximally relative to the sleeve. In some embodiments, a plurality of pins can be spaced longitudinally along the inner surface of the sleeve 332 to provide incremental locking at a plurality of discrete points along the length of the sleeve. As yet another example, teeth, pins, hooks, barbs, or other structures can be deployed from the shaft 312 to engage the sleeve 332 or vice versa to lock movement therebetween. Such structures can be biased to deploy automatically or can be manually deployed, for example by an elongated rod inserted through a cannulation of the shaft to push the structures out into engagement with the sleeve 332.

The shank 302, receiver member 304, and closure mechanism 308 can include any of the features of the corresponding components of the bone anchor 100 described above. For example, as shown, the receiver member 304 can be polyaxially coupled to the head 310 of the shank 302 and can include a pair of spaced apart arms 314A, 314B defining a recess 316 therebetween. The closure mechanism 308 can be positionable between and can engage the arms 314A, 314B to capture a spinal fixation element, e.g., a spinal rod 306, within the receiver member 304, to fix the spinal fixation element with respect to the receiver member, and to fix the receiver member with respect to the shank 302.

In use, the bone anchor 300 can be initially configured such that the inner telescoping portion 330 is disposed in a distal position with respect to the outer telescoping portion 332, as shown in FIG. 3A. For example, the shaft 312 can be threaded all the way into the sleeve 332 to bottom out the shaft in the sleeve. A driver instrument can be applied to the head 310 of the anchor portion 302 to rotate the anchor portion about the axis A1. The inner and outer telescoping portions 330, 332 can be rotationally fixed to one another in at least one rotation al direction and at least in the initial configuration such that torque applied to the inner telescoping portion is in turn applied to the outer telescoping portion to drive the anchor portion 302 into bone B. For example, bottoming out the shaft 312 in the sleeve 332 can allow torque to be applied to the sleeve via the shaft in one rotational direction, e.g., in a clockwise or tightening direction.

Once the anchor portion 302 is driven to the target depth, or at any other desired time, the length L of the bone anchor 300 can be adjusted to achieve optimal positioning between the receiver member 304 and a spinal rod 306. The length can be adjusted by rotating the driver instrument in an opposite direction to back the shaft 312 out of the outer sleeve 332. The torque required to rotate the shaft 312 relative to the sleeve 332 can be less than the torque required to loosen the sleeve 332 from the bone B, such that counter-rotation of the driver is effective to lift the shaft proximally 312 without loosening the sleeve from the bone. When the receiver member 304 is positioned at the desired height, the rod 306 can be inserted into the receiver member and the closure mechanism 308 can be applied to secure the rod, as shown in FIG. 3C. In the illustrated embodiment, a set screw 308 is threaded into extension tabs 328 that extend proximally from the arms 314A, 314B of the receiver member 304 and is advanced distally within the receiver member until the rod 306 is securely fastened to the bone anchor 300, as shown in FIG. 3D, at which point the reduction tabs 328 can be removed.

The bone anchor 300 can allow the length L of the bone anchor to be adjusted independently of adjusting an angle between the receiver member 304 and the shank 302. The bone anchor 300 can allow the length L of the bone anchor to be adjusted at a location other than the interface between the receiver member 304 and the shank 302. The bone anchor 300 can allow the length L of the bone anchor to be adjusted, and/or can allow the rod to be moved towards the receiver member, without disturbing the anchor-bone interface, e.g., without moving the thread 338 relative to the bone.

It will thus be appreciated that the above process allows the length L of the bone anchor 300 to be adjusted in situ such that the receiver member 304 can be moved proximally towards the rod 306 instead of or in addition to forcing the rod distally towards the receiver member. By reducing or eliminating the need to reduce the rod 306 distally relative to the anchor portion 302, reduction forces applied to the anchor-bone interface can be reduced, thereby improving the strength and stability of the implanted construct. This can also reduce or eliminate the need to precisely contour the rod 306 to the bone anchor 300, simplifying the surgical procedure.

Figure 4A:
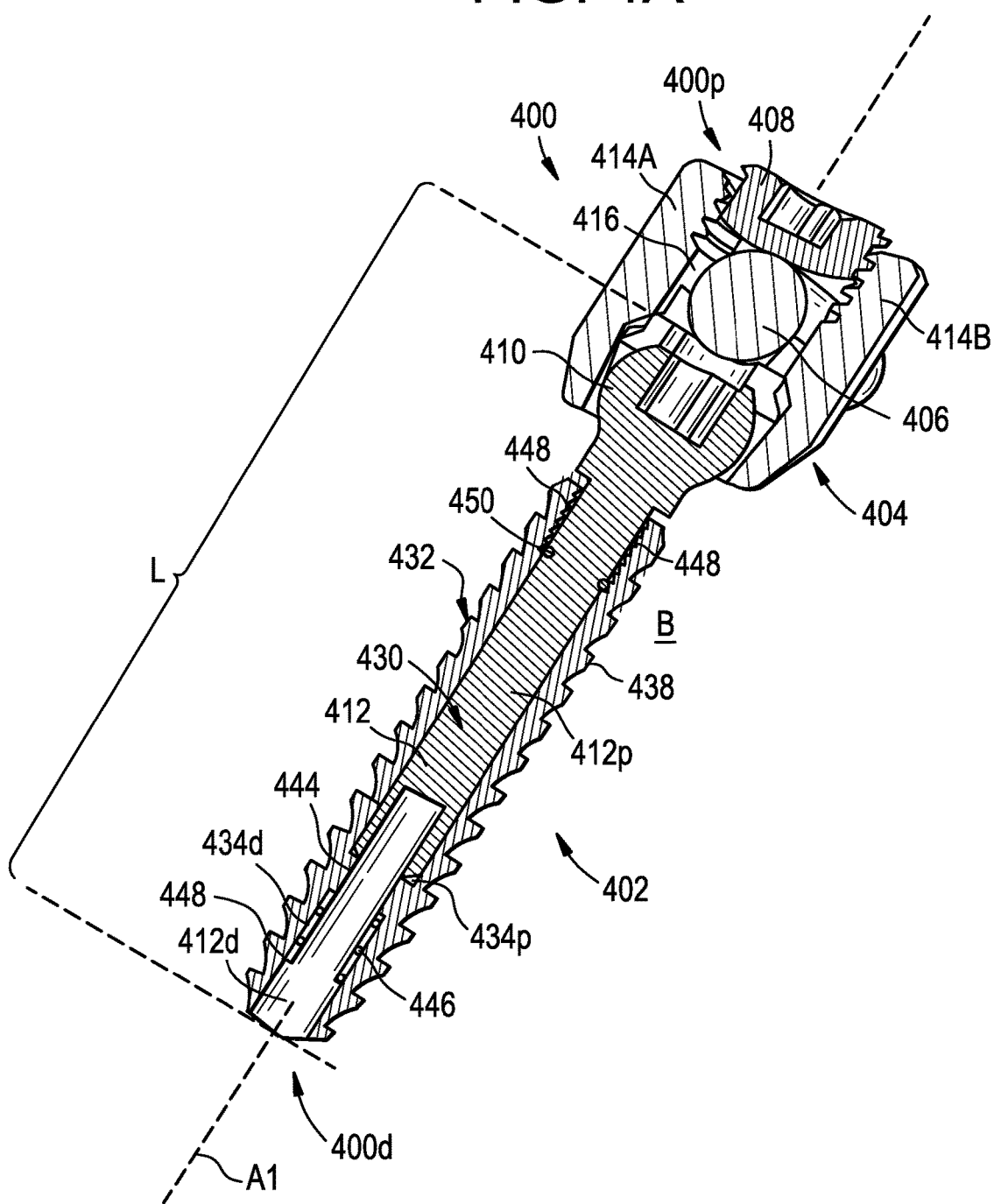
FIG. 4A is a sectional perspective view of a longitudinally-adjustable bone anchor and a spinal rod.
Figure 4B:
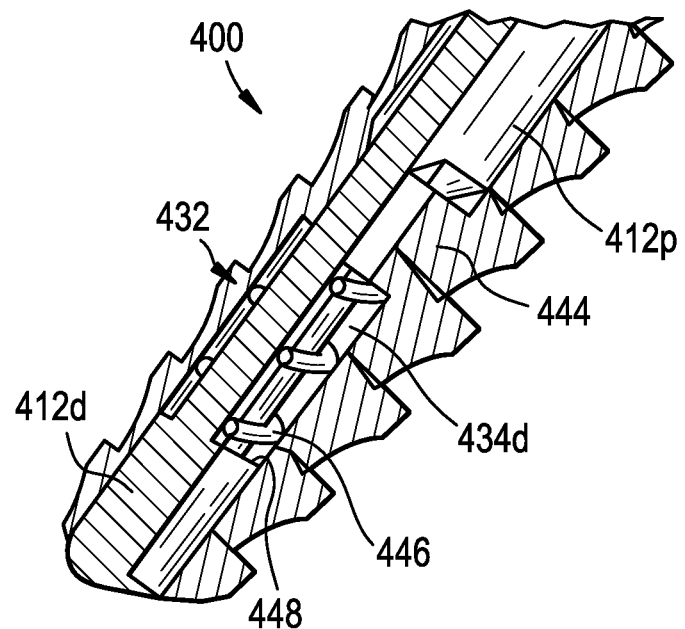
FIG. 4B is a sectional perspective detail view of the distal end of the bone anchor of FIG. 4A.
Figure 4C:
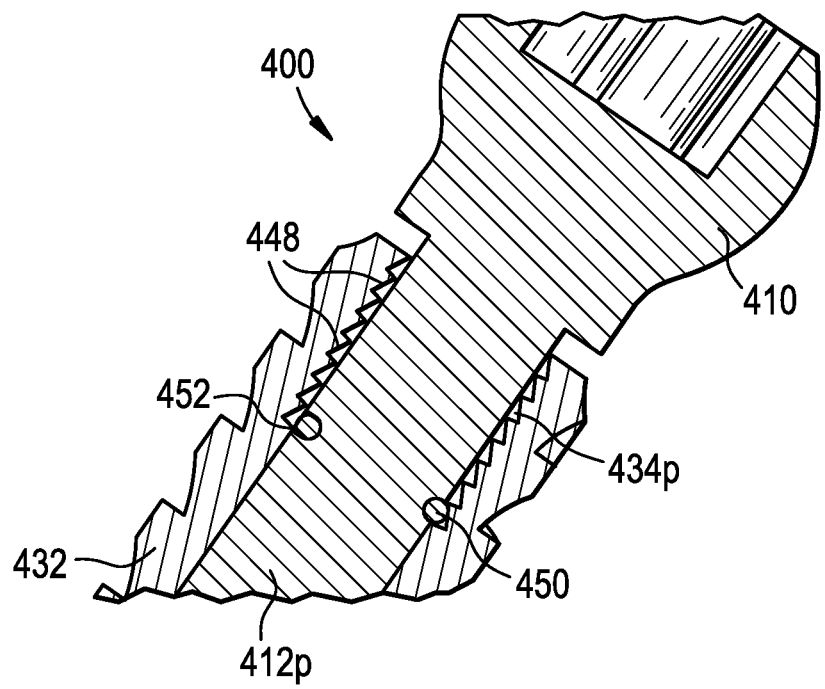
FIG. 4C is a sectional perspective detail view of the proximal end of the bone anchor of FIG. 4A.

FIGS. 4A-4C illustrate an exemplary embodiment of a longitudinally-adjustable bone anchor 400. The bone anchor 400 can include a proximal end 400p and a distal end 400d that define a proximal-distal or longitudinal axis A1 extending therebetween. The bone anchor 400 can be longitudinally-adjustable or expandable such that a length L of the bone anchor, defined between a distal-most tip of the bone anchor and a proximal rod seat of the bone anchor, can be modified. The bone anchor 400 can be adjustable in situ, e.g., after implanting in bone, or prior to being implanted.

The bone anchor 400 can include an anchor portion or shank 402, a head or receiver member 404, and a closure mechanism 408.

The shank 402 can include inner and outer telescoping portions 430, 432 movable with respect to one another to adjust the length L of the bone anchor 400. In the illustrated embodiment, the outer telescoping portion 432 includes a sleeve that defines a proximal inner cavity 434p and a distal inner cavity 434d. The proximal and distal cavities 434p, 434d can be separated by an annular projection 444. The cavities 434p, 434d can be sized to receive at least a portion of the inner telescoping portion 430 therein. The sleeve 432 can include a cannulation to allow the sleeve to be delivered over a guidewire or to allow a flowable material to be delivered through a distal tip of the sleeve and into surrounding bone. An outer surface of the sleeve 432 can include a bone-engaging thread 438. A bias element or spring 446 configured to bias the inner telescoping portion 430 in a distal direction relative to the outer telescoping portion 432 can be disposed in the distal cavity 434d. A series of ratchet teeth 448 or other locking features can be formed in an inner sidewall of the proximal cavity 434p. The ratchet teeth 448 can be engaged with a locking ring 450 to selectively lock the inner telescoping portion 430 at any of a plurality of discrete longitudinal positions along the outer telescoping portion 432.

The inner telescoping portion 430 can include a shaft 412 mounted in the sleeve 432 and a proximal head 410 to which the receiver member 404 can be coupled. The shaft 412 can be slidably disposed within the cavity 434 to allow the shaft to translate longitudinally with respect to the sleeve 432. The shaft 412 can be free to rotate about the axis A1 relative to the sleeve 432, or rotation between the shaft and the sleeve can be limited or completely restricted. Various features for restricting rotation can be used. For example, the sleeve 432 can include a transverse pin or a ridge that is received in a slot or groove formed in the shaft 412 to allow the shaft to translate longitudinally relative to the sleeve but to prevent the shaft from rotating relative to the sleeve. In other arrangements, the pin or ridge can be included in the inner shaft 412 and the slot or groove can be formed in the outer sleeve 432. The shaft 412 can include a cannulation that extends longitudinally therethrough, e.g., to allow the shaft to be delivered over a guidewire or to allow a flowable material to be delivered through the shaft and into the cavity 434 or into bone in which the bone anchor 400 is implanted.

The shaft 412 can include a proximal portion 412p and a distal portion 412d. The proximal and distal portions 412p, 412d can be formed integrally with one another or can be separate components joined together using any of a variety of known techniques such as an adhesive, a weld, a threaded interface, and so forth. The proximal shaft 412p can be slidably disposed in the proximal cavity 434p. Distal travel of the proximal shaft 412p relative to the sleeve 432 can be limited by the projection 444.

The distal shaft 412d can include a reduced-diameter proximal portion configured to slide through a central aperture defined by the projection 444 and an enlarged-diameter distal portion configured to abut the projection 444 to limit proximal movement of the shaft 412 relative to the sleeve 432, e.g., to prevent the shaft from being removed proximally from the sleeve during use. The bias element 446 can be disposed between the projection 444 and a shoulder 448 formed on the distal shaft 412d. The bias element 446 can be effective to bias the distal shaft 412d, and the proximal shaft 412p attached thereto, distally relative to the outer sleeve 432. This can help prevent inadvertent longitudinal extension of the bone anchor 400, e.g., during shipping, sterilization, or handling prior to surgery.

The bone anchor 400 can include a locking element configured to selectively lock longitudinal movement between the shaft 412 and the sleeve 432. The locking element can be configured to prevent distal movement of the shaft 412 relative to the sleeve 432, to prevent proximal movement of the shaft relative to the sleeve, or to prevent both distal and proximal movement of the shaft relative to the sleeve.

In the illustrated embodiment, the locking element includes a ring 450 seated within an annular groove 452 formed in an outer surface of the proximal shaft 412p and corresponding ratchet teeth 448 formed in the sleeve 432.

The ring 450 can protrude from the groove 452 to engage the ratchet teeth 448 formed in the proximal cavity 434p.

A proximally-directed force applied along the axis A1 can cause the shaft 412 to translate longitudinally relative to the sleeve 432. As the shaft 412 slides within the sleeve, the ring 450 can slide along an inclined surface of the ratchet tooth with which it is presently engaged, eventually snapping into an adjacent recess formed by the next successive ratchet tooth. The ring 450 can be configured to deform or compress radially-inward towards the groove 452 during this process. For example, the ring 450 can be a C-clip or can include slits, grooves, or webbing to facilitate radial deformation. Alternatively, or in addition, the ratchet teeth 448 or the sleeve 432 can deform or expand. The above process can be repeated any number of times as desired by the user to selectively position and lock the inner shaft 412 at any of a plurality of discrete longitudinal positions along the outer sleeve 432, thereby adjusting the length L of the bone anchor 400.

While the ring 450 and the teeth 448 are formed at a proximal end of the anchor portion 402, it will be appreciated that they can alternatively be formed at a distal end thereof or at any location along the length of the anchor portion 402. The illustrated teeth 448 define unidirectional ramping surfaces, such that the teeth prevent distal movement of the shaft 412 but allow proximal movement when sufficient force is applied thereto to deform the ring 450. In other embodiments, the teeth can be ramped in an opposite direction, or can be ramped in both directions.

While a locking ring 450 and ratchet teeth 448 are shown, it will be appreciated that various other locking elements can be used instead or in addition. For example, a flowable material can be delivered through a cannulation of the shaft 412 to fill the void space left in the cavity 434 once the shaft is translated proximally relative to the sleeve 432. The flowable material can be a curable material configured to solidify within the cavity 434 to lock movement between the shaft 412 and the sleeve 432. Exemplary materials include cements, adhesives, and the like. As another example, the sleeve 432 can include one or more spring-loaded pins configured to deploy into the cavity 434 as the shaft 412 is translated proximally relative to the sleeve. In some embodiments, a plurality of pins can be spaced longitudinally along the inner surface of the sleeve 432 to provide incremental locking at a plurality of discrete points along the length of the sleeve. As yet another example, teeth, pins, hooks, barbs, or other structures can be deployed from the shaft 412 to engage the sleeve 432 to lock movement therebetween. Such structures can be biased radially outward from the shaft 412. Alternatively, or in addition, such structures can be deployed from the shaft 412 by inserting an elongated rod through a cannulation of the shaft to push the structures out into engagement with the sleeve 432.

The shank 402, receiver member 404, and closure mechanism 408 can include any of the features of the corresponding components of the bone anchor 100 described above. For example, as shown, the receiver member 404 can be polyaxially coupled to the head 410 of the shank 402 and can include a pair of spaced apart arms 414A, 414B defining a recess 416 therebetween. The closure mechanism 408 can be positionable between and can engage the arms 414A, 414B to capture a spinal fixation element, e.g., a spinal rod 406, within the receiver member 404, to fix the spinal fixation element with respect to the receiver member, and to fix the receiver member with respect to the shank 402.

In use, the bone anchor 400 can be initially configured such that the inner telescoping portion 430 is disposed in a distal position with respect to the outer telescoping portion 432, as shown in FIG. 4A. In the initial configuration, the locking ring 450 can be seated in a relatively distal position along the length of the ratchet teeth 448. A driver instrument can be applied to the head 410 of the anchor portion 402 to rotate the anchor portion about the axis A1. The inner and outer telescoping portions 430, 432 can be rotationally fixed to one another at least in the initial configuration such that torque applied to the inner telescoping portion is in turn applied to the outer telescoping portion to drive the anchor portion 402 into bone B.

Once the anchor portion 402 is driven to the target depth, or at any other desired time, a spinal rod 406 can be positioned in the receiver member 404 and the closure mechanism 408 can be applied to secure the rod, as shown in FIG. 4A. In the illustrated embodiment, a set screw 408 is threaded into the arms 414A, 414B of the receiver member 404.

As the set screw 408 is tightened to reduce the rod 406 into the receiver member 404, the inner telescoping portion 430 can be pulled proximally such that it translates longitudinally with respect to the outer telescoping portion 432 while the outer telescoping portion remains at a fixed longitudinal position with respect to the surrounding bone B. As the inner telescoping portion 430 moves proximally, the locking ring 450 traverses one or more of the ratchet teeth 448, snapping into engagement with each successive groove defined between the teeth. The set screw 408 can be advanced distally within the receiver member 404 until the rod 406 is securely fastened to the bone anchor 400. The shaft 412 at this time is disposed in a final position along the sleeve 432, locked from translating distally by the interaction between the ring 450 and the teeth 448.

The bone anchor 400 can allow the length L of the bone anchor to be adjusted independently of adjusting an angle between the receiver member 404 and the shank 402. The bone anchor 400 can allow the length L of the bone anchor to be adjusted at a location other than the interface between the receiver member 404 and the shank 402. The bone anchor 400 can allow the length L of the bone anchor to be adjusted, and/or can allow the rod to be moved towards the receiver member, without disturbing the anchor-bone interface, e.g., without moving the thread 438 relative to the bone.

It will thus be appreciated that the above process allows the length L of the bone anchor 400 to be adjusted in situ such that the receiver member 404 can be pulled proximally towards the rod 406 instead of or in addition to forcing the rod distally towards the receiver member. By reducing or eliminating the need to reduce the rod 406 distally relative to the anchor portion 402, reduction forces applied to the anchor-bone interface can be reduced, thereby improving the strength and stability of the implanted construct. This can also reduce or eliminate the need to precisely contour the rod 406 to the bone anchor 400, simplifying the surgical procedure.

FIGS. 5A-5F illustrate an exemplary embodiment of a longitudinally-adjustable bone anchor 500. The bone anchor 500 can include a proximal end 500p and a distal end 500d that define a proximal-distal or longitudinal axis A1 extending therebetween. The bone anchor 500 can be longitudinally-adjustable or expandable such that a length L of the bone anchor, defined between a distal-most tip of the bone anchor and a proximal rod seat of the bone anchor, can be modified. The bone anchor 500 can be adjustable in situ, e.g., after implanting in bone, or prior to being implanted.

The bone anchor 500 can include an anchor portion or shank 502, a head or receiver member 504, and a closure mechanism 508.

The shank 502 can include inner and outer telescoping portions 530, 532 movable with respect to one another to adjust the length L of the bone anchor 500. In the illustrated embodiment, the outer telescoping portion 532 includes a sleeve that defines an inner cavity 534. The cavity 534 can be sized to receive at least a portion of the inner telescoping portion 530 therein. The cavity 534 can include a closed or substantially-closed distal end and an open proximal end. The sleeve 532 can include a cannulation 536 that extends from the cavity 534 to the distal tip of the sleeve, e.g., to allow the sleeve to be delivered over a guidewire or to allow a flowable material to be delivered through a distal tip of the sleeve and into surrounding bone. An outer surface of the sleeve 532 can include a bone-engaging thread 538.

The inner telescoping portion 530 can include a distal shaft 512 mounted in the cavity 534 of the sleeve 532 and a proximal head 510 to which the receiver member 504 can be coupled. The distal shaft 512 can be slidably disposed within the cavity 534 to allow the distal shaft to translate longitudinally with respect to the sleeve 532. The distal shaft 512 can be free to rotate about the axis A1 relative to the sleeve 532, or rotation between the shaft and the sleeve can be limited or completely restricted. Various features for restricting rotation can be used. For example, the sleeve 532 can include a transverse pin or a ridge that is received in a slot or groove formed in the shaft 512 to allow the shaft to translate longitudinally relative to the sleeve but to prevent the shaft from rotating relative to the sleeve. In other arrangements, the pin or ridge can be included in the inner shaft 512 and the slot or groove can be formed in the outer sleeve 532. The shaft 512 can include a cannulation that extends longitudinally therethrough, e.g., to allow the shaft to be delivered over a guidewire or to allow a flowable material to be delivered through the shaft and into the cavity 534 or into bone in which the bone anchor 500 is implanted.

The bone anchor 500 can include one or more stops configured to limit the degree to which the shaft 512 can translate longitudinally relative to the sleeve 532. For example, the bone anchor 500 can include a shoulder, pin, or other feature at a proximal end of the sleeve 532 to prevent the shaft 512 from being removed proximally from the sleeve during use.

The bone anchor 500 can include a locking element configured to selectively lock longitudinal movement between the shaft 512 and the sleeve 532. The locking element can be configured to prevent distal movement of the shaft 512 relative to the sleeve 532, to prevent proximal movement of the shaft relative to the sleeve, or to prevent both distal and proximal movement of the shaft relative to the sleeve.

In the illustrated embodiment, the locking element includes one or more tabs 540 configured to lock relative movement between the shaft 512 and the sleeve 532 when a distally-directed force is applied thereto, e.g., by tightening a set screw 508. Each tab 540 can have a proximal end and a distal end aligned generally parallel with the axis A1. The proximal end of the tab 540 can project into the rod recess 516 of the receiver member 504 such that the tab interferes with the set screw 508 as the set screw is tightened. The tab 540 can extend through an opening formed in the respective arm 514A, 514B of the receiver member such that the distal end of the tab is positioned outside of the rod recess 516. Instead of extending through an opening in the receiver member 504, the tabs 540 can be disposed entirely on the exterior of the receiver member 504 and can be engaged with an alternative closure mechanism, such as a nut that extends around the outer circumference of the receiver member. The distal end of the tab 540 can engage with the shaft 512, the sleeve 532, or both the shaft and the sleeve to lock one or more motion degrees of freedom between the shaft and the sleeve.

For example, the distal end of the tab 540 can be tapered in a proximal-distal direction to define a wedge that is at least partially inserted between the shaft 512 and the sleeve 532. As the set screw 508 is tightened, each tab 540 can translate distally to drive the wedge deeper between the shaft and the sleeve to lock movement between said components.

As another example, the distal end of the tab 540 can be initially folded, bent, or deformed radially-inward, as shown in FIGS. 5A and 5B. Resilient or shape memory material properties of the tabs 540 can cause the tabs to be biased away from the folded position towards a deployed position shown in FIGS. 5C and 5D. Accordingly, as the receiver member 504 and shaft 512 are lifted proximally relative to the sleeve 532, the tabs 540 can spring down from the folded position to contact a proximal-facing surface of the sleeve 532 and act as vertical supports to maintain the receiver member 504 at an elevated position relative to the sleeve 532. In another arrangement, a force applied to the proximal end of the tab 540 by the set screw 508 can release the tab 540 from the folded position and allow it to spring into the deployed position.

While opposed tabs 540 are shown, it will be appreciated that various other locking elements can be used instead or in addition. For example, a flowable material can be delivered through a cannulation of the shaft 512 to fill the void space left in the cavity 534 once the shaft is translated proximally relative to the sleeve 532. The flowable material can be a curable material configured to solidify within the cavity 534 to lock movement between the shaft 512 and the sleeve 532. Exemplary materials include cements, adhesives, and the like. As another example, the sleeve 532 can include one or more spring-loaded pins configured to deploy into the cavity 534 as the shaft 512 is translated proximally relative to the sleeve. In some embodiments, a plurality of pins can be spaced longitudinally along the inner surface of the sleeve 532 to provide incremental locking at a plurality of discrete points along the length of the sleeve. As yet another example, teeth, pins, hooks, barbs, or other structures can be deployed from the shaft 512 to engage the sleeve 532 to lock movement therebetween. Such structures can be biased radially outward from the shaft 512. Alternatively, or in addition, such structures can be deployed from the shaft 512 by inserting an elongated rod through a cannulation of the shaft to push the structures out into engagement with the sleeve 532.

The shank 502, receiver member 504, and closure mechanism 508 can include any of the features of the corresponding components of the bone anchor 100 described above. For example, as shown, the receiver member 504 can be polyaxially coupled to the head 510 of the shank 502 and can include a pair of spaced apart arms 514A, 514B defining a recess 516 therebetween. The closure mechanism 508 can be positionable between and can engage the arms 514A, 514B to capture a spinal fixation element, e.g., a spinal rod 506, within the receiver member 504, to fix the spinal fixation element with respect to the receiver member, and to fix the receiver member with respect to the shank 502.

In use, the bone anchor 500 can be initially configured such that the inner telescoping portion 530 is disposed in a distal position with respect to the outer telescoping portion 532, as shown in FIG. 5A. In the initial configuration, the locking element (e.g., the tabs 540) can be in a retracted or disengaged position. A driver instrument can be applied to the head 510 of the anchor portion 502 to rotate the anchor portion about the axis A1. The inner and outer telescoping portions 530, 532 can be rotationally fixed to one another at least in the initial configuration such that torque applied to the inner telescoping portion is in turn applied to the outer telescoping portion to drive the anchor portion 502 into bone B.

Once the anchor portion 502 is driven to the target depth, or at any other desired time, a spinal rod 506 can be positioned in the receiver member 504 and the closure mechanism 508 can be applied to secure the rod, as shown in FIG. 5B. In the illustrated embodiment, a set screw 508 is threaded into extension tabs 528 that extend proximally from the arms 514A, 514B of the receiver member 504.

As the set screw 508 is tightened to reduce the rod 506 into the receiver member 504, as shown in FIG. 5C, the inner telescoping portion 530 can be pulled proximally such that it translates longitudinally with respect to the outer telescoping portion 532 while the outer telescoping portion remains at a fixed longitudinal position with respect to the surrounding bone B. The set screw 508 can be advanced distally within the receiver member 504 until the rod 506 is securely fastened to the bone anchor 500, as shown in FIG. 5D, and the reduction tabs 528 can be removed. As the set screw 508 is tightened, the locking element (e.g., the tabs 540) can be deployed or engaged to lock the relative longitudinal positions of the inner and outer telescoping portions 530, 532.

The bone anchor 500 can allow the length L of the bone anchor to be adjusted independently of adjusting an angle between the receiver member 504 and the shank 502. The bone anchor 500 can allow the length L of the bone anchor to be adjusted at a location other than the interface between the receiver member 504 and the shank 502. The bone anchor 500 can allow the length L of the bone anchor to be adjusted, and/or can allow the rod to be moved towards the receiver member, without disturbing the anchor-bone interface, e.g., without moving the thread 538 relative to the bone.

It will thus be appreciated that the above process allows the length L of the bone anchor 500 to be adjusted in situ such that the receiver member 504 can be pulled proximally towards the rod 506 instead of or in addition to forcing the rod distally towards the receiver member. By reducing or eliminating the need to reduce the rod 506 distally relative to the anchor portion 502, reduction forces applied to the anchor-bone interface can be reduced, thereby improving the strength and stability of the implanted construct. This can also reduce or eliminate the need to precisely contour the rod 506 to the bone anchor 500, simplifying the surgical procedure.

FIGS. 6A-6D illustrate an exemplary embodiment of a longitudinally-adjustable bone anchor 600, shown with a spinal rod 606. The bone anchor 600 can include a proximal end 600p and a distal end 600d that define a proximal-distal or longitudinal axis A1 extending therebetween. The bone anchor 600 can be longitudinally-adjustable or expandable such that a length L of the bone anchor, defined between a distal-most tip of the bone anchor and a proximal rod seat of the bone anchor, can be modified. The bone anchor 600 can be adjustable in situ, e.g., after implanting in bone, or prior to being implanted.

The bone anchor 600 can include an anchor portion or shank 602, a head or receiver member 604, a closure mechanism 608, and one or more spacers or risers 654. In use, the spacer 654 can be positioned in the receiver member 604 to increase the height of the rod seat and thereby extend the length L of the bone anchor 600.

The shank 602, receiver member 604, and closure mechanism 608 can include any of the features of the corresponding components of the bone anchor 100 described above. For example, as shown, the receiver member 604 can be polyaxially coupled to the head 610 of the shank 602 and can include a pair of spaced apart arms 614A, 614B defining a recess 616 therebetween. The closure mechanism 608 can be positionable between and can engage the arms 614A, 614B to capture a spinal fixation element, e.g., a spinal rod 606, within the receiver member 604, to fix the spinal fixation element with respect to the receiver member, and to fix the receiver member with respect to the shank 602.

The spacer 654 can extend across at least a portion of the rod seat of the receiver member 604. The spacer 654 can include a distal facing surface 654d that mimics the distal facing surface of a spinal fixation or stabilization element with which the bone anchor assembly 600 is to be used. For example, in the case of a cylindrical spinal rod 606, the distal-facing surface 654d of the spacer 654 can define a section of a cylinder having a radius equal to or substantially equal to the diameter of the spinal rod. The proximal-facing surface 654p of the spacer 654 can define a seat configured to receive the spinal fixation or stabilization element therein. In the illustrated embodiment, the seat 654p is sized and shaped to receive a cylindrical spinal rod 606 therein. The radius of curvature of the proximal-facing seat 654p can be equal to or substantially equal to that of the rod-receiving channel 616 of the receiver member 604.

The spacer 654 can include features for preventing movement of the spacer with respect to the receiver member 604 in one or more degrees of freedom. For example, as shown, the spacer can include one or more protrusions 656 that engage an outer sidewall of the receiver member 604 to prevent translation of the spacer 654 along a rod or spacer axis A2 with respect to the receiver member. The protrusions 656 can extend from the distal-facing surface 654d of the spacer 654 as shown, or can extend from side surfaces of the spacer or any other surface of the spacer. The protrusions 656 can be convexly curved as shown to eliminate sharp edges that could irritate surrounding tissue. The protrusions 656 can include inwardly-facing planar surfaces 658 that engage corresponding outwardly-facing planar surfaces 660 of the receiver member 604. Alternatively, or in addition, the spacer 654 can include protrusions that engage an inner surface of the receiver member 604, or other features for preventing or limiting axial translation of the spacer relative to the receiver member along the axis A2. In some embodiments, the spacer 654 can include features for limiting or preventing rotation of the spacer relative to the receiver member 604 about the axis A2. For example, at least a portion 662 of the sidewalls of the spacer 654 can be planar and can engage corresponding planar portions 664 of the rod-receiving recess 616 of the receiver member 604 to prevent rotation of the spacer about the axis A2 relative to the receiver member. The spacer 654 can be snap-fit, friction-fit, or otherwise reversibly mated to the receiver member 604, e.g., to help retain the spacer 654 in place prior to inserting and locking the rod 606.

When the bone anchor 600 is assembled, the spacer can be positioned between the opposed arms 614A, 614B of the receiver member 604 such that the spacer 654 is seated within the rod-receiving recess 616 of the receiver member. The spinal rod 606 can then be seated on the proximal-facing surface 654p of the spacer 654, between the opposed arms 614A, 614B of the receiver member 604, and locked in place with the closure mechanism 608 as described above.

A kit can be provided including a plurality of spacers 654, each having a different height in the proximal-distal direction, or each having a different rod-seat radius, etc., to give the user flexibility in selecting the length L of the bone anchor 600 and the diameter of the rod with which the bone anchor 600 is used. FIG. 6B illustrates a spacer 654 having a height H1 and FIG. 6C illustrates a spacer 654' having a height H2 that is greater than H1.

In some cases, the thickness of the spacer 654 can cause the spinal rod 606 to be raised up within the receiver member 604 to a degree that prevents sufficient attachment of the closure mechanism 608 or prevents attachment of the closure mechanism altogether. In such cases, the bone anchor assembly 600 can include a cap 666, e.g., of the type shown in FIG. 6D. The cap 666 can attach to the proximal end of the receiver member 604. The cap 666 can include a threaded central opening sized to receive the closure mechanism 608. Accordingly, the cap 666 can functionally extend the height of the threaded portion of the receiver member 604 to accommodate both the rod 606 and the spacer 654 between the rod seat of the receiver member 604 and the closure mechanism 608. The illustrated cap 666 includes a generally U-shaped channel sized to accommodate the spinal rod 606 defined by opposed arms 668A, 668B. The cap 666 can be attached to the receiver member 604 in any of a variety of ways. For example, the cap 666 can include one or more projections, e.g., formed on an inner surface of the arms 668A, 668B that engage with a corresponding one or more recesses formed in the receiver member 604, or the receiver member can include one or more projections that engage with a corresponding one or more recesses formed in the cap. As the closure mechanism 608 is tightened, the middle portion of the cap 666 can flex proximally, pulling projections formed on inner surface of the arms 668A, 668B tightly into engagement with the receiver member 604. The cap 666 can snap fit onto the receiver member 604. The cap 666 can slide onto the receiver member 604 from the side with a tongue and groove or dovetail connection. The cap 666 can lock onto the receiver member 604 by a quarter-turn rotation of the cap relative to the receiver member. The distal-facing underside of the cap 666 can form a negative of the proximal end of the receiver member 604 to limit or prevent rotation of the cap relative to the receiver member about the axis A1. The proximal-facing surface of the cap 666 can be convexly curved or domed to eliminate sharp edges that could irritate surrounding tissue.

In use, the bone anchor 600 can be implanted in bone using standard techniques. A driver instrument can be applied to the head 610 of the anchor portion 602 to rotate the anchor portion about the axis A1 and drive the anchor portion into bone B.

Figure 6A:
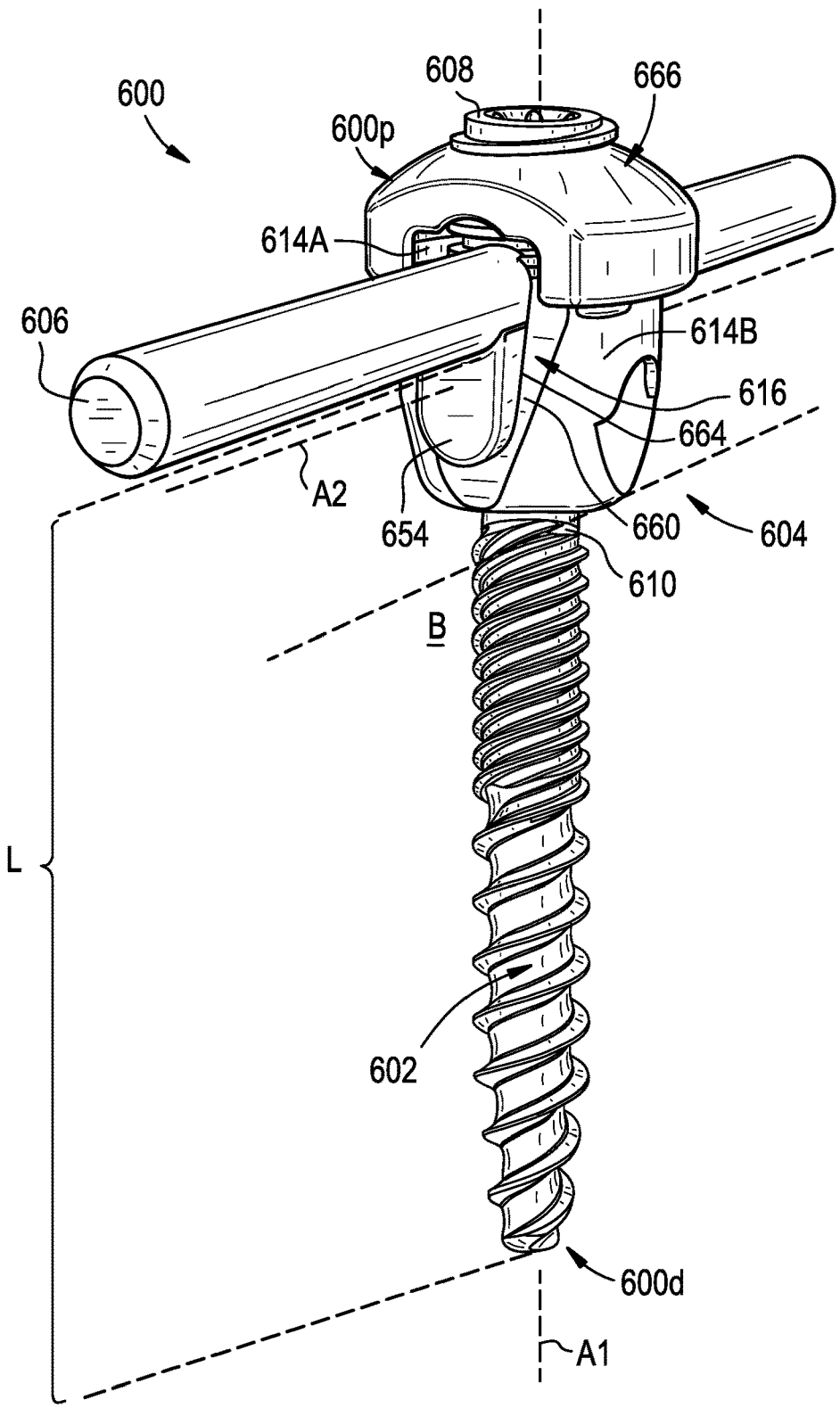
FIG. 6A is a perspective view of a longitudinally-adjustable bone anchor and a spinal rod.
Figure 6B:
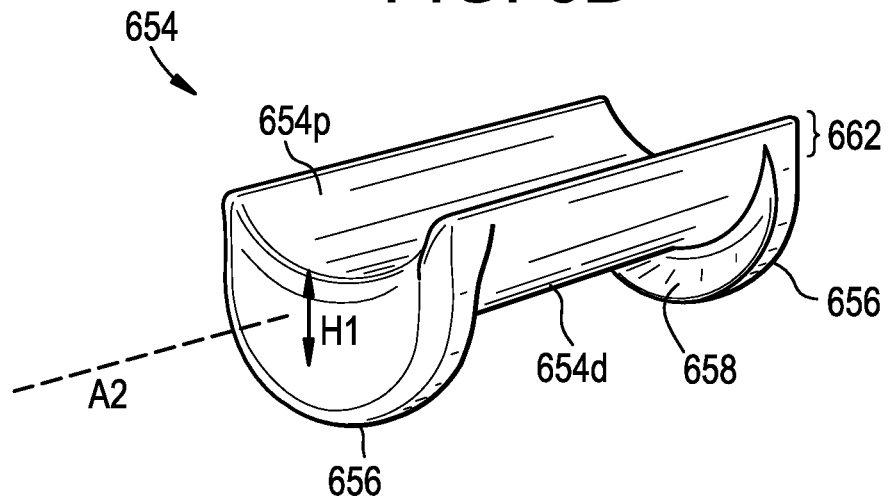
FIG. 6B is a perspective view of a spacer that can be used with the bone anchor of FIG. 6A.
Figure 6C:
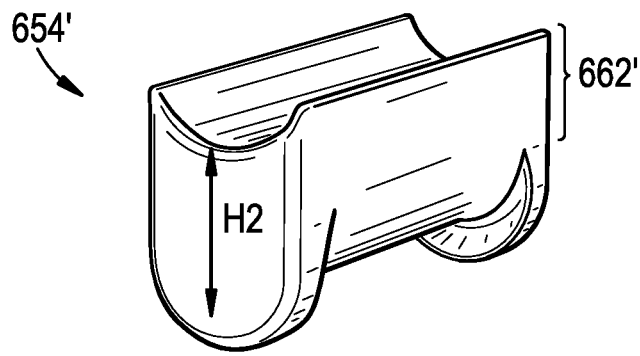
FIG. 6C is a perspective view of another spacer that can be used with the bone anchor of FIG. 6A, having a height greater than that of the spacer of FIG. 6B.
Figure 6D:
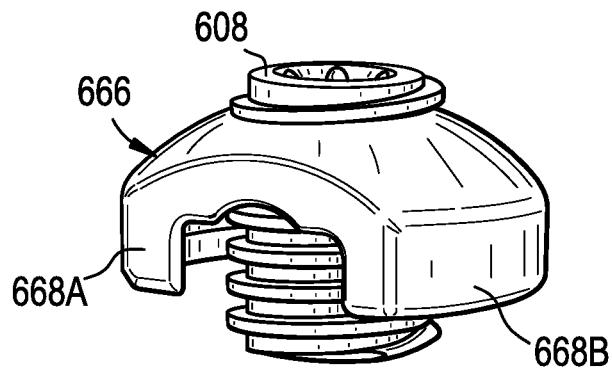
FIG. 6D is a perspective view of a closure mechanism and cap of the bone anchor of FIG. 6A.

Once the anchor portion 602 is driven to the target depth, or at any other desired time, a spacer 654 and a spinal rod 606 can be positioned in the receiver member 604 and the closure mechanism 608 can be applied to secure the spacer and the rod, as shown in FIG. 6A. This process can include test fitting the rod 606 to the bone anchor 600 and determining an optimal spacer height. A spacer 654 that most closely matches the determined height can be selected from among a plurality of spacers, e.g., provided as part of a kit. As another example, a plurality of spacers having different heights can be test fit to the bone anchor 600 until the desired bone anchor length L is achieved. In some embodiments, multiple spacers can be stacked on top of one another within the receiver member 604 to achieve the desired bone anchor length L. In some embodiments, the spacers can be formed from a trimmable or shavable material to allow the height of the spacer to be adjusted or fine-tuned during the surgical procedure. Exemplary spacer materials include metals such as titanium, polymers such as PEEK, elastomers such as silicone, materials known to be biocompatible or suitable for surgical applications, and/or any of a variety of other materials. The spacer 654 can have a height H measured between the proximal and distal surfaces 654$p$, 654$d$ in the range of about 0.5 mm to about 50 mm, in the range of about 1 mm to about 10 mm, and/or in the range of about 1 mm to about 5 mm. The spacer can have a height H of about 5 mm, about 4 mm, about 3 mm, about 2 mm, or about 1 mm. The ratio of the height of the spacer to the length of the shank portion 602 can be in the range of about 5% to about 100%, in the range of about 10% to about 50%, and/or in the range of about 15% to about 30%.

With the spinal rod 606 and the desired spacer 654 assembled to the receiver member 604, the set screw 608 can be advanced distally within the receiver member 604 until the rod 606 is securely fastened to the bone anchor 600.

The bone anchor 600 can allow the length L of the bone anchor to be adjusted independently of adjusting an angle between the receiver member 604 and the shank 602. The bone anchor 600 can allow the length L of the bone anchor to be adjusted at a location other than the interface between the receiver member 604 and the shank 602. The bone anchor 600 can allow the length L of the bone anchor to be adjusted, and/or can allow the rod to be seated in the receiver member, without disturbing the anchor-bone interface, e.g., without moving a thread of the anchor portion 602 relative to the bone.

It will thus be appreciated that the above process allows the length L of the bone anchor 600 to be adjusted in situ such that the effective height of the receiver member 604 can be moved or adjusted proximally towards the rod 606 instead of or in addition to forcing the rod distally towards the receiver member. By reducing or eliminating the need to reduce the rod 606 distally relative to the anchor portion 602, reduction forces applied to the anchor-bone interface can be reduced, thereby improving the strength and stability of the implanted construct. This can also reduce or eliminate the need to precisely contour the rod 606 to the bone anchor 600, simplifying the surgical procedure.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The bone anchors 200, 300, 400, 500, 600 disclosed herein can be longitudinally-adjustable over a variety of lengths L. In some embodiments, the bone anchors can be longitudinally-extended by a length in the range of about 0.5 mm to about 50 mm, in the range of about 1 mm to about 10 mm, and/or in the range of about 1 mm to about 5 mm. The bone anchors can be longitudinally-extended by a length about 5 mm, about 4 mm, about 3 mm, about 2 mm, or about 1 mm. The ratio of the amount by which the length of the bone anchors can be extended to the non-extended length of the shank portion can be in the range of about 5% to about 100%, in the range of about 10% to about 50%, and/or in the range of about 15% to about 30%.

While the methods illustrated and described herein generally involve attaching spinal rods to multiple vertebrae, it will be appreciated that the bone anchors herein can be used with various other types of fixation or stabilization hardware, in any bone, in non-bone tissue, or in non-living or non-tissue objects. The bone anchors disclosed herein can be fully implanted, or can be used as part of an external fixation or stabilization system. The devices and methods disclosed herein can be used in minimally-invasive surgery and/or open surgery.

The devices disclosed herein and the various component parts thereof can be constructed from any of a variety of known materials. Exemplary materials include those which are suitable for use in surgical applications, including metals such as stainless steel, titanium, or alloys thereof, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

Although specific embodiments are described above, it should be understood that numerous changes may be made within the spirit and scope of the concepts described.

The invention claimed is:

1. A longitudinally-adjustable bone anchor, comprising:
   a receiver member that defines a rod-receiving recess;
   a shank having inner and outer telescoping portions, the outer telescoping portion of the shank including a bone-engaging thread and defining an inner cavity, the inner telescoping portion including a shaft disposed in the cavity of the outer telescoping portion and a head that movably couples the shank to the receiver member; and
   a locking element configured to selectively prevent distal movement of the inner telescoping portion relative to the outer telescoping portion, to prevent proximal movement of the inner telescoping portion relative to the outer telescoping portion, or to prevent both proximal and distal movement of the inner telescoping portion relative to the outer telescoping portion,
   wherein the locking element comprises one or more tabs extending from the receiver member, and
   wherein the inner and outer telescoping portions are longitudinally-adjustable relative to one another to adjust a length of the bone anchor.

2. The bone anchor of claim 1, wherein the inner telescoping portion is constrained from rotating axially relative to the outer telescoping portion.

3. The bone anchor of claim 1, wherein the inner telescoping portion is threaded into the cavity of the outer telescoping portion.

4. The bone anchor of claim 1, wherein the locking element comprises one or more biased teeth configured to project radially inward from an inner sidewall of the cavity to engage the shaft as the shaft is moved proximally within the cavity.

5. The bone anchor of claim 1, wherein the locking element comprises a threaded engagement between the inner and outer telescoping portions.

6. The bone anchor of claim 1, wherein the locking element comprises a locking ring disposed around the shaft of the inner telescoping portion and configured to engage ratchet teeth spaced longitudinally along an inner surface of the cavity.

7. The bone anchor of claim 1, wherein the cavity includes proximal and distal portions separated by an annular projection.

8. The bone anchor of claim 7, wherein the shaft is biased distally relative to the outer telescoping portion by a spring disposed between the annular projection and a shoulder formed on the shaft.

9. The bone anchor of claim 1, wherein the tabs are configured to wedge between the inner and outer telescoping portions when a distally-directed force is applied to the tabs.

10. The bone anchor of claim 1, wherein tightening a closure mechanism to the receiver member applies a distally-directed force to the tabs.

11. The bone anchor of claim 1, wherein each of the tabs has a folded position and a deployed position, the tabs in the deployed position being configured to contact the outer telescoping portion and support the receiver member in an elevated position relative to the outer telescoping portion.

12. A longitudinally-adjustable bone anchor, comprising:
    a receiver member that defines a rod-receiving channel having a first rod seat;
    a threaded shank movably coupled to the receiver member; and
    a spacer disposed in the rod-receiving channel of the receiver member and having a distal surface that contacts the first rod seat and a proximal surface that defines a second rod seat spaced a distance apart from the first rod seat,
    wherein the spacer includes one or more protrusions that engage an outer sidewall of the receiver member to prevent translation of the spacer relative to the receiver member along a longitudinal axis of the spacer.

13. The bone anchor of claim 12, wherein the first rod seat is defined by opposed U-shaped recesses formed in the receiver member.

14. The bone anchor of claim 12, wherein the distal surface of the spacer is a section of a cylinder.

15. The bone anchor of claim 12, wherein the proximal surface of the spacer is a section of a cylinder.

16. The bone anchor of claim 12, wherein the protrusions extend from the distal surface of the spacer.

17. The bone anchor of claim 12, wherein the protrusions are convexly curved.

18. The bone anchor of claim 12, wherein the protrusions include inwardly-facing planar surfaces that engage corresponding outwardly-facing planar surfaces of the receiver member.

19. The bone anchor of claim 12, wherein the spacer includes opposed planar sidewalls connecting the proximal and distal surfaces of the spacer that engage respective opposed planar sidewalls of the rod-receiving channel.

20. A longitudinally-adjustable bone anchor, comprising:
    a receiver member that defines a rod-receiving recess;
    a shank having inner and outer telescoping portions, the outer telescoping portion of the shank including a bone-engaging thread and defining an inner cavity, the inner telescoping portion including a shaft disposed in the cavity of the outer telescoping portion and a head that movably couples the shank to the receiver member;
    wherein the inner and outer telescoping portions are longitudinally-adjustable relative to one another to adjust a length of the bone anchor, and
    wherein the inner telescoping portion is constrained from rotating axially relative to the outer telescoping portion by a geometric interface between an outer portion of the inner telescoping portion and an inner portion of the outer telescoping portion.

21. A longitudinally-adjustable bone anchor, comprising:
a receiver member that defines a rod-receiving recess;
a shank having inner and outer telescoping portions, the outer telescoping portion of the shank including a bone-engaging thread and defining an inner cavity, the inner telescoping portion including a shaft disposed in the cavity of the outer telescoping portion and a head that movably couples the shank to the receiver member;
wherein the inner and outer telescoping portions are longitudinally-adjustable relative to one another to adjust a length of the bone anchor,
wherein the cavity includes proximal and distal portions separated by an annular projection, and
wherein the shaft is biased distally relative to the outer telescoping portion by a spring disposed between the annular projection and a shoulder formed on the shaft, the shaft extending proximally through the spring and the annular projection.

* * * * *